United States Patent [19]
Miyazawa et al.

[11] Patent Number: 5,879,585
[45] Date of Patent: Mar. 9, 1999

[54] LIQUID CRYSTALLINE COMPOUND HAVING ALKYNYL GROUP, AND LIQUID CRYSTAL COMPOSITIONS AND LIQUID CRYSTAL DISPLAY DEVICE THEREFROM

[75] Inventors: Kazutoshi Miyazawa; Shuichi Matsui; Hiroyuki Takeuchi; Yasuhiro Kubo; Fusayuki Takeshita; Etsuo Nakagawa, all of Chiba, Japan

[73] Assignee: Chisso Corporation, Osaka-fu, Japan

[21] Appl. No.: 948,516

[22] Filed: Oct. 10, 1997

[30] Foreign Application Priority Data

Oct. 16, 1996 [JP] Japan ................................ 8-294491
Jun. 24, 1997 [JP] Japan ................................ 9-183144

[51] Int. Cl.$^6$ .......................... C09K 19/52; C09K 19/34; C09K 19/30; C07C 15/54
[52] U.S. Cl. .............................. 252/299.01; 252/299.61; 252/299.63; 252/299.66; 252/299.67; 585/534
[58] Field of Search ................. 252/299.01, 299.61, 252/299.63, 299.66, 299.67; 585/534

[56] References Cited

FOREIGN PATENT DOCUMENTS

| | | |
|---|---|---|
| 0727473 | 8/1996 | European Pat. Off. . |
| 4441963 | 11/1995 | Germany . |
| 56-4522 | 1/1981 | Japan . |
| 59-196803 | 11/1984 | Japan . |
| 3-258741 | 11/1991 | Japan . |
| 4-282354 | 10/1992 | Japan . |
| 5-43503 | 2/1993 | Japan . |
| 5-140042 | 6/1993 | Japan . |
| 5-507725 | 11/1993 | Japan . |
| 7-18022 | 1/1995 | Japan . |
| WO90/13610 | 11/1990 | WIPO . |

OTHER PUBLICATIONS

WPIDS 93–216716, 1993.
WPIDS 95–093876, 1995.
Buchecker et al, "Synthesis, Physical Properties and Structural Relationships of New, End–Chain Substituted Nematic Liquid Crystals", Mol. Cryst. Liq. Cryst., 1987, vol. 149, pp. 359–373.

Petrzilka, "Polar Acetylenic Liquid Crystals with Broad Mesomorphic Ranges. The Positional Influence of Different C,C–Elements on the Transition Temperatures", Mol. Cryst. Liq. Cryst., 1984, vol. 111, pp. 329–346.

Primary Examiner—Shean C. Wu
Attorney, Agent, or Firm—Wenderoth, Lind & Ponack, L.L.P.

[57] ABSTRACT

A liquid crystalline compound having a remarkably high Δn and good miscibility with other liquid crystalline compounds, and expressed by the general formula (1)

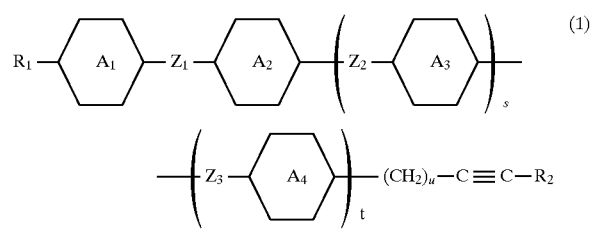

wherein $R_1$ represents, for example, a halogen atom, cyano group, or an alkyl or alkenyl group of 1 to 15 carbon atoms in which alkyl or alkenyl group hydrogen atom may be replaced, for example, by fluorine atom, and one or not-adjacent two or more methylene groups may be replaced by oxygen atom, —CH=CH— or —C≡C—; $R_2$ represents an alkyl group of 1 to 10 carbon atoms or hydrogen atom; rings $A_1$, $A_2$, $A_3$, and $A_4$ independently represent, for example, 1,4-cyclohexylene or 1,4-phenylene in which hydrogen atom may be replaced by a halogen atom or cyano group; $Z_1$, $Z_2$, and $Z_3$ independently represent, for example, a covalent bond or —CH$_2$CH$_2$—; s and t are 0 or 1; u is an integer of 1 to 5; and each of the elements in the general formula may be its isotope. A liquid crystal composition and a liquid crystal display device using the compound are also disclosed.

28 Claims, No Drawings

LIQUID CRYSTALLINE COMPOUND HAVING ALKYNYL GROUP, AND LIQUID CRYSTAL COMPOSITIONS AND LIQUID CRYSTAL DISPLAY DEVICE THEREFROM

TECHNICAL FIELD

The present invention relates to a novel liquid crystalline compound having alkynyl group as a side chain, a liquid crystal composition comprising the compound, and a liquid crystal display device comprising the composition.

BACKGROUND ART

Liquid crystal display devices utilize optical (refractive) anisotropy and dielectric anisotropy of liquid crystal materials. Liquid crystal display devices have widely been used for the display of watches, word processors, computer terminals, and televisions. Liquid crystal materials mean principally liquid crystal compounds exhibiting a liquid crystal phase. These materials have been used in a form of a composition in which various kind of compounds are usually mixed. At that time when the composition is produced, compounds which do not exhibit by themselves a liquid crystal phase, but can exhibit a liquid crystal property when mixed with a liquid crystal compound or liquid crystal composition and thus clearly have a latent liquid crystallinity are also useful. For purpose of the present invention, the term "liquid crystalline compounds" include the latter compounds having a latent liquid crystallinity in addition to the liquid crystal compounds.

While various properties are required of liquid crystal compositions, optical anisotropy ($\Delta n$) is one of especially important properties. Since when the product ($\Delta n \cdot d$) of the $\Delta n$ and cell thickness (d) is a specific value (first minimum or second minimum), display qualities (contrast and viewing angle) of liquid crystal display devices become optimum, cells now being practically used have been designed according to the optimum value. However, in order to satisfy other required performances up to maximum, several different values are sometimes selected for d under the conditions described above. For instance, increase of response speed is strongly required lately, and there is a trend toward a small d with an improvement in cell preparation technology for a background to satisfy the requirement. Accordingly, exploitation of liquid crystal compositions having a high optical anisotropy, namely, exploitation of liquid crystalline compounds which can achieve a high optical anisotropy have been demanded.

Heretofore, compounds expressed by any one of the formulas (10) to (12) are disclosed, as liquid crystal compounds having a comparatively high $\Delta n$, in Laid-open Japanese Patent Publication No. Sho 61-5031, Mol. Cryst. Liq. Cryst., 48, 175 (1978), or Laid-open Japanese Patent Publication No. Hei 2-180,840.

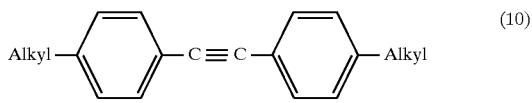

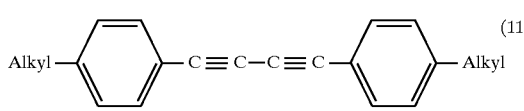

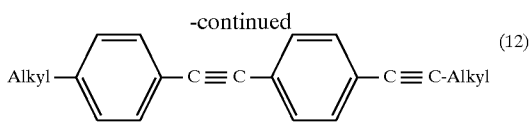

However, compounds expressed by the formula (10) do not exhibit a sufficiently high $\Delta n$. Whereas compounds expressed by the formula (12) exhibit a comparatively high $\Delta n$, the compounds are considerably poor in miscibility with other liquid crystalline compounds. Whereas compounds expressed by the formula (11) exhibit a comparatively high $\Delta n$ and good miscibility, the compounds are considerably poor in chemical stability and have such a problem that they are naturally decomposed even when allowed to stand at room temperature.

DISCLOSURE OF THE INVENTION

An object of the present invention is to solve the problems in the art described above. Another object of the present invention is to provide liquid crystalline compounds having a good miscibility with other liquid crystalline compounds in addition to a remarkably high $\Delta n$; liquid crystal compositions comprising the compound; and liquid crystal display devices comprising the composition.

In order to achieve the objects described above, the present invention has the following aspects:

(1) A liquid crystalline compound expressed by the general formula (1)

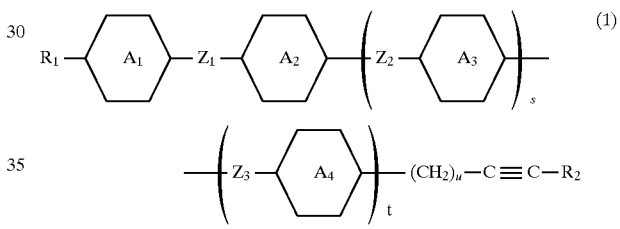

wherein $R_1$ represents a halogen atom, cyano group, or an alkyl group, alkenyl group, alkynyl group, alkoxy group, alkoxyalkyl group, alkenyloxy group, alkynyloxy group, or alkadienyl group having 1 to 15 carbon atoms in which group (excluding cyano group) hydrogen atom may be replaced by fluorine atom, chlorine atom, or cyano group, and one or not-adjacent two or more methylene groups may be replaced by oxygen atom, —CH=CH— or —C≡C—; $R_2$ represents an alkyl group having 1 to 10 carbon atoms or hydrogen atom; rings $A_1$, $A_2$, $A_3$, and $A_4$ independently represent 1,4-cyclohexylene or 1,4-phenylene, 1,3-dioxane-2,5-diyl, pyridine-2,5-diyl, or pyrimidine-2,5-diyl in all of which hydrogen atom may be replaced by a halogen atom or cyano group; $Z_1$, $Z_2$, and $Z_3$ independently represent a covalent bond, —CH$_2$CH$_2$—, —CH=CH—, —C≡C—, —CH$_2$O—, —OCH$_2$—, —(CH$_2$)$_4$-, —(CH$_2$)$_3$—O—, —O—(CH$_2$)$_3$-, —(CH$_2$)$_2$—CH=CH—, —CH=CH—(CH$_2$)$_2$-, —C≡C—CH=CH—, —CH=CH—C≡C—, —CF$_2$O—, —OCF$_2$—, —CF=CF—, —CO$_2$—, or —OCO—; s and t are independently an integer of 0 or 1; u is an integer of 1 to 5; and each of the elements in the general formula may be its isotope.

(2) The liquid crystalline compound recited in the aspect (1) described above wherein $R_1$ is an alkyl group, alkenyl group, alkynyl group, or alkoxy group; and both s and t are 0.

(3) The liquid crystalline compound recited in the aspect (1) described above wherein $R_1$ is an alkyl group, alkenyl group, alkynyl group, or alkoxy group; s is 1; and t is 0.

(4) The liquid crystalline compound recited in the aspect (1) described above wherein $R_1$ is an alkyl group, alkenyl group, alkynyl group, or alkoxy group; and both s and t are 1.

(5) The liquid crystalline compound recited in the aspect (2) described above wherein both rings $A_1$ and $A_2$ are 1,4-cyclohexylene; and $Z_1$ is a covalent bond or —CH=CH—.

(6) The liquid crystalline compound recited in the aspect (2) described above wherein ring $A_2$ is 1,4-phenylene in which hydrogen atom may be replaced by a halogen atom; ring $A_1$ is 1,4-cyclohexylene, 1,4-phenylene, 1,3-dioxane-2,5-diyl, pyridine-2,5-diyl, or pyrimidine-2,5-diyl in all of which hydrogen atom may be replaced by a halogen atom; and $Z_1$ is a covalent bond or —CF=CF—.

(7) The liquid crystalline compound recited in the aspect (3) described above wherein ring $A_3$ is 1,4-cyclohexylene; and $Z_1$ and $Z_2$ are independently a covalent bond, —CH$_2$CH$_2$—, —CH=CH—, —C≡C—, or —CF=CF—.

(8) The liquid crystalline compound recited in the aspect (3) described above wherein ring $A_3$ is 1,4-phenylene in which hydrogen atom may be replaced by a halogen atom; and $Z_1$ and $Z_2$ are independently a covalent bond, —CH$_2$CH$_2$—, —CH=CH—, —C≡C—, or —CF=CF—.

(9) The liquid crystalline compound recited in the aspect (4) described above wherein ring $A_4$ is 1,4-cyclohexylene; and $Z_1$, $Z_2$, and $Z_3$ are independently a covalent bond, —CH$_2$CH$_2$—, —CH=CH—, —C≡C=, or —CF=CF—.

(10) The liquid crystalline compound recited in the aspect (4) described above wherein ring $A_4$ is 1,4-phenylene in which hydrogen atom may be replaced by a halogen atom; and $Z_1$, $Z_2$, and $Z_3$ are independently a covalent bond, —CH$_2$CH$_2$—, —CH=CH—, —C≡C—, or —CF=CF—.

(11) A liquid crystal composition comprising at least one liquid crystalline compound recited in any one of the aspects (1) to (10) described above.

(12) A liquid crystal composition comprising, as a first component, at least one liquid crystalline compound recited in any one of the aspects (1) to (10) described above, and comprising, as a second component, at least one compound selected from the group consisting of the compounds expressed by any one of the general formulas (2), (3), and (4)

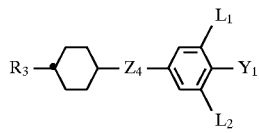

(2)

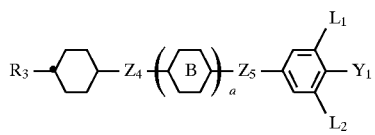

(3)

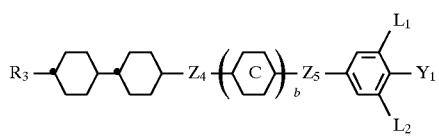

(4)

wherein $R_3$ represents an alkyl group having 1 to 10 carbon atoms in which group one or not-adjacent two or more methylene groups may be replaced by oxygen atom or —CH=CH—, and any hydrogen atom may be replaced by fluorine atom; $Y_1$ represents fluorine atom, chlorine atom, —OCF$_3$, —OCF$_2$H, —CF$_3$, —CF$_2$H, —CFH$_2$, —OCF$_2$CF$_2$H, or —OCF$_2$CFHCF$_3$; $L_1$ and $L_2$ independently represent hydrogen atom or fluorine atom; $Z_4$ and $Z_5$ independently represent —CH$_2$CH$_2$—, —(CH$_2$)$_4$-, —CO$_2$—, —CF$_2$O—, —OCF$_2$—, —CH=CH—, or a covalent bond; ring B represents 1,4-cyclohexylene, 1,3-dioxane-2,5-diyl, or 1,4-phenylene in which phenylene any hydrogen atom may be replaced by fluorine atom; ring C represents 1,4-cyclohexylene, or 1,4-phenylene in which phenylene any hydrogen atom may be replaced by fluorine atom; a and b are independently 0 or 1; and each of the elements in the general formulas may be its isotope.

(13) A liquid crystal composition comprising, as a first component, at least one liquid crystalline compound recited in any one of the aspects (1) to (10) described above, and comprising, as a second component, at least one compound selected from the group consisting of the compounds expressed by the general formula (5) or (6)

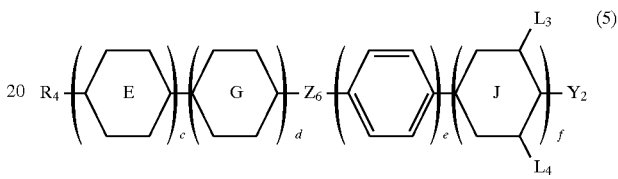

(5)

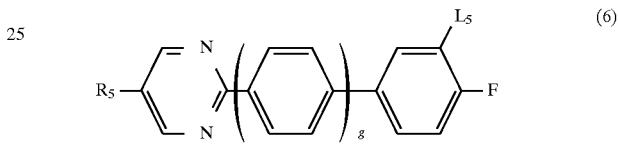

(6)

wherein $R_4$ and $R_5$ independently represent an alkyl group having 1 to 10 carbon atoms in which group one or not-adjacent two or more methylene groups may be replaced by oxygen atom or —CH=CH—, and any hydrogen atom may be replaced by fluorine atom; $Y_2$ represents —CN group or —C≡C—CN; ring E represents 1,4-cyclohexylene, 1,4-phenylene, 1,3-dioxane-2,5-diyl, or pyrimidine-2,5-diyl; ring G represents 1,4-cyclohexylene, 1,4-phenylene in which phenylene hydrogen atom may be replaced by fluorine atom, or pyrimidine-2,5-diyl; ring J represents 1,4-cyclohexylene or 1,4-phenylene, $Z_6$ represents —CH$_2$CH$_2$—, —CO$_2$—, or a covalent bond; $L_3$, $L_4$, and $L_5$ independently represent hydrogen atom or fluorine atom; c, d, e, f, and g are independently 0 or 1; and each of the elements in the general formulas may be its isotope.

(14) A liquid crystal composition comprising, as a first component, at least one liquid crystalline compound recited in any one of the aspects (1) to (10) described above, comprising, as a second component, at least one compound selected from the group consisting of the compounds expressed by any one of the general formulas (2), (3), and (4) recited in the aspect (12) described above, and comprising, as a third component, at least one compound selected from the group consisting of the compounds expressed by any one of the general formulas (7), (8), and (9)

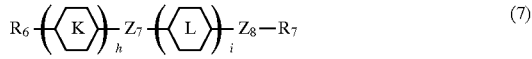

(7)

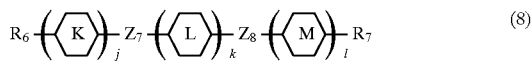

(8)

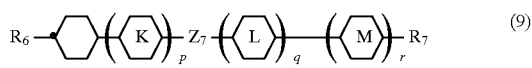

(9)

wherein $R_6$ and $R_7$ independently represent an alkyl group having 1 to 10 carbon atoms in which group one or not-adjacent two or more methylene groups may be replaced by oxygen atom or —CH═CH—, and any hydrogen atom may be replaced by fluorine atom; rings K, L, and M independently represent 1,4-cyclohexylene, pyrimidine-2,5-diyl, or 1,4-phenylene in which phenylene hydrogen atom may be replaced by fluorine atom; $Z_7$ and $Z_8$ independently represent —C≡C—, —$CO_2$—, —$CH_2CH_2$—, —CH═CH—, or a covalent bond; h to l, and p to r are independently 0 or 1; and each of the elements in the general formulas may be its isotope.

(15) A liquid crystal composition comprising, as a first component, at least one liquid crystalline compound recited in any one of the aspects (1) to (10) described above, comprising, as a second component, at least one compound selected from the group consisting of the compounds expressed by the general formula (5) or (6) recited in the aspect (13) described above, and comprising, as a third component, at least one compound selected from the group consisting of the compounds expressed by any one of the general formulas (7), (8), and (9) recited in the aspect (14) described above.

(16) A liquid crystal composition comprising, as a first component, at least one liquid crystalline compound recited in any one of the aspects (1) to (10) described above, comprising, as a part of a second component, at least one compound selected from the group consisting of the compounds expressed by any one of the general formulas (2), (3), and (4) recited in the aspect (12) described above, comprising, as another part of the second component, at least one compound selected from the group consisting of the compounds expressed by the general formula (5) or (6) recited in the aspect (13) described above, and comprising, as a third component, at least one compound selected from the group consisting of the compounds expressed by any one of the general formulas (7), (8), and (9) recited in the aspect (14) described above.

(17) The liquid crystal composition according to the aspect (11) described above wherein the liquid crystal composition further comprises an optically active compound.

(18) The liquid crystal composition according to the aspect (12) described above wherein the liquid crystal composition further comprises an optically active compound.

(19) The liquid crystal composition according to the aspect (13) described above wherein the liquid crystal composition further comprises an optically active compound.

(20) The liquid crystal composition according to the aspect (14) described above wherein the liquid crystal composition further comprises an optically active compound.

(21) The liquid crystal composition according to the aspect (15) described above wherein the liquid crystal composition further comprises an optically active compound.

(22) The liquid crystal composition according to the aspect (16) described above wherein the liquid crystal composition further comprises an optically active compound.

(23) A liquid crystal display device comprising the liquid crystal composition recited in any one of the aspects (11) to (22) described above.

BEST MODE FOR CARRYING OUT THE INVENTION

Liquid crystalline compounds of the present invention expressed by the general formula (1) are characterized by having alkynyl group expressed by the formula (20) as a side chain

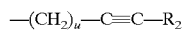

wherein u and $R_2$ have the same meaning as those described above.

By having such side chain at a terminal of compound, liquid crystalline compounds of the present invention have an extremely high Δn; besides the compounds have a good miscibility with other liquid crystalline compounds. Thus, it was confirmed that the liquid crystalline compounds can preferably be used, as component, for liquid crystal compositions even for STN (super twisted nematic) which have most generally been used.

In the general formula (1) described above, $R_1$ represents the atoms and groups mentioned above, and a halogen atom, cyano group, and an alkyl group, alkoxy group, alkoxyalkyl group, alkenyl group, alkenyloxy group, alkynyl group, alkynyloxy group, haloalkyl group, haloalkoxy group, haloalkenyl group, haloalkynyl group, and alkadienyl group can broadly be mentioned as its examples.

More specifically, fluorine atom and chlorine atom as halogen atom;

methyl group, ethyl group, propyl group, butyl group, pentyl group, hexyl group, heptyl group, octyl group, nonyl group, and decyl group as alkyl group;

methoxy group, ethoxy group, propoxy group, butoxy group, pentoxy group, hexyloxy group, and heptyloxy group as alkoxy group;

methoxymethyl group and ethoxymethyl group as alkoxyalkyl group;

vinyl group, propenyl group, butenyl group, pentenyl group, hexenyl group, heptenyl group, and octenyl group as alkenyl group;

propenyloxy group, butenyloxy group, pentenyloxy group, hexenyloxy group, heptenyloxy group, and octenyloxy group as alkenyloxy group;

ethynyl group, propynyl group, butynyl group, pentynyl group, hexynyl group, heptynyl group, and octynyl group as alkynyl group;

propynyloxy group, butynyloxy group, pentynyloxy group, hexynyloxy group, heptynyloxy group, and octynyloxy group as alkynyloxy group;

fluoromethyl group, difluoromethyl group, trifluoromethyl group, fluoroethyl group, difluoroethyl group, trifluoroethyl group, tetrafluoroethyl group, perfluoroethyl group, fluoropropyl group, difluoropropyl group, trifluoropropyl group, tetrafluoropropyl group, hexafluoropropyl group, fluorobutyl group, fluoropentyl group, and fluorohexyl group as haloalkyl group;

difluoromethoxy group, trifluoromethoxy group, fluoroethoxy group, difluoroethoxy group, trifluoroethoxy group, tetrafluoroethoxy group, perfluoroethoxy group, fluoropropoxy group, difluoropropoxy group, trifluoropropoxy group, tetrafluoropropoxy group, hexafluoropropoxy group, fluorobutoxy group, fluoropentoxy group, and fluorohexyloxy group as haloalkoxy group;

fluorovinyl group, fluoropropenyl group, fluorobutenyl group, and fluoropentenyl group as haloalkenyl group;

trifluoroalkynyl group and difluoroalkynyl group as haloalkynyl group; and butadienyl group, pentadienyl group, hexadienyl group, heptadienyl group, and octadienyl group as alkadienyl group can be mentioned, respectively.

Among these $R_1$, an alkyl group having 1 to 6 carbon atoms and an alkoxy group having 1 to 5 carbon atoms are preferable for achieving a low viscosity. As their examples, methyl group, ethyl group, propyl group, butyl group, pentyl group, hexyl group, methoxy group, ethoxy group, propoxy group, butoxy group, and pentoxy group can be mentioned, but those groups excluding hexyl group and methoxy group are particularly preferable.

In order to achieve a high dielectric anisotropy ($\Delta\epsilon$), a halogen atom, cyano group, a haloalkyl group, and a haloalkoxy group are preferable. As their examples, fluorine atom and chlorine atom can be mentioned for halogen atom;

fluoromethyl group, difluoromethyl group, trifluoromethyl group, 2-fluoroethyl group, 1,1-difluoroethyl group, 2,2-difluoroethyl group, 2,2,2-trifluoroethyl group, 1,1,2,2-etrafluoroethyl group, perfluoroethyl group, 3-fluoropropyl group, 2,2-difluoropropyl group, 3,3-difluoropropyl group, 3,3,3-trifluoropropyl group, 2,2,3,3-tetrafluoropropyl group, 1,1,2,3,3,3-hexafluoropropyl group, 1,1,2,2,3,3-hexafluoropropyl group, 4-fluorobutyl group, and 5-fluoropentyl group can be referred for haloalkyl group; and difluoromethoxy group, trifluoromethoxy group, 2-fluoroethoxy group, 2,2-difluoroethoxy group, 2,2,2-trifluoroethoxy group, 1,1,2,2-tetrafluoroethoxy group, perfluoroethoxy group, 3-fluropropoxy group, 3,3-difluoropropoxy group, 3,3,3-trifluoropropoxy group, 1,1,2,3,3,3-hexafluoropropoxy group, 4-fluorobutoxy group, and 5-fluoropentoxy group can be stated for haloalkoxy group.

Among the haloalkyl groups mentioned above, fluoromethyl group, difluoromethyl group, trifluoromethyl group, 2-fluoroethyl group, 1,1-difluoroethyl group, 2,2-difluoroethyl group, 2,2,2-trifluoroethyl group, 3-fluoropropyl group, 2,2-difluoropropyl group, 4-fluorobutyl group, and 5-fluoropentyl group; and among the haloalkoxy groups mentioned above, difluoromethoxy group, trifluoromethoxy group, 2-fluoroethoxy group, 2,2-difluoroethoxy group, 2,2,2-trifluoroethoxy group, 1,1,2,2-tetrafluoroethoxy group, 3-fluoropropoxy group, 3,3,3-trifluoropropoxy group, 1,1,2,3,3,3-hexafluoropropoxy group, and 4-fluorobutoxy group are especially preferable.

In order to achieve a large ratio of elastic constants ($K_{33}/K_{11}$), an alkenyl group and alkenyloxy group, particularly, 1E-alkenyl group, 2Z-alkenyl group, 3E-alkenyl group, and an alkadienyl group are preferable. For instance, vinyl group, 3-butenyl group, 2-fluorovinyl group, and 2,2-difluorovinyl group as alkenyl group;

2-propenyloxy group and 2E-butenyloxy group as alkenyloxy group;

1E-propenyl group, 1E-butenyl group, 1E-pentenyl group, 1E-hexenyl group, 3-fluoro-1E-propenyl group, 4-fluoro-1E-butenyl group, and 5-fluoro-1E-pentenyl group as 1E-alkenyl group;

2Z-butenyl group as 2Z-alkenyl group;

3E-pentenyl group and 3E-hexenyl group as 3E-alkenyl group; and butadienyl group, 1,4-pentadienyl group, 1,5-hexadienyl group, and 1,5-heptadienyl group as alkadienyl group can be mentioned.

As the alkenyl groups mentioned above, the groups mentioned as examples are all preferable; and particularly, 2-propenyloxy group as alkenyloxy group;

1E-propenyl group, 1E-butenyl group, 1E-pentenyl group, and 4-fluoro-1E-butenyl group as 1E-alkenyl group;

3E-pentenyl group as 3E-alkenyl group; and 1,5-hexadienyl group and 1,5-heptadienyl group as alkadienyl group are preferable, respectively.

In order to achieve a higher $\Delta n$, an alkynyl group and alkynyloxy group are preferable. For instance, ethynyl group, 1-propynyl group, 2-propynyl group, 2-butynyl group, 3-butynyl group, 3-pentynyl group, 3,3,3-trifluoro-1-propynyl group, 3,3-difluoro-1-propynyl group, and 2-cyanoethynyl group as alkynyl group; and 3-butynyloxy group as alkynyloxy group can be mentioned, respectively.

Next, groups represented by rings $A_1$ to $A_4$ in the general formula (1) are described. As their specific examples, 1,4-cyclohexylene, 1-cyano-1,4-cyclohexylene, 1,4-phenylene, 2-fluoro-1,4-phenylene, 2-chloro-1,4-phenylene, 2,3-difluoro-1,4-phenylene, 2,3-dichloro-1,4-phenylene, 2,5-difluoro-1,4-phenylene, 2,6-difluoro-1,4-phenylene, 1,3-dioxane-2,5-diyl, 5-cyano-1,3-dioxane-2,5-diyl, pyridine-2,5-diyl, 3-fluoropyridine-2,5-diyl, 5-fluoropyridine-2,5-diyl, 6-fluoropyridine-2,5-diyl, pyrimidine-2,5-diyl, and 3-fluoropyrimidine-2,5-diyl can be mentioned. When properties of liquid crystal compositions to be obtained are taken into account, 1,4-cyclohexylene, 1,4-phenylene, 2-fluoro-1,4-phenylene, 2,3-difluoro-1,4-phenylene, 1,3-dioxane-2,5-diyl, pyridine-2,5-diyl, and pyrimidine-2,5-diyl are preferable.

Also, the groups represented by $Z_1$ to $Z_3$ are described above. When properties of liquid crystal compositions to be obtained are taken into account, a covalent bond, $-CH_2CH_2-$, $-CH=CH-$, $-C\equiv C-$, $-CH_2O-$, $-OCH_2-$, $-CF_2O-$, $-OCF_2-$, $-CF=CF-$, $-CO_2-$, and $-OCO-$ are preferable, and a covalent bond, $-CH_2CH_2-$, $-CH=CH-$, $-C\equiv C-$, $-CF_2O-$, $-OCF_2-$, and $-CF=CF-$ are more desirable.

In the general formula (1), s and t independently represent 0 or 1. Accordingly, when both s and t are 0, the general formula (1) indicates two-ring system compounds; when one of s and t is 1, and the other is 0, it does three-ring system compounds; and when both s and t are 1, it indicates four-ring system compounds.

While u is an integer of 1 to 5, 2 to 5 is preferable and 2 to 4 is more desirable to provide more chemically stable liquid crystalline compounds.

$R_2$ is a terminal group of an alkynyl group, as a side chain, expressed by the formula (20). While $R_2$ is selected from an alkyl group having 1 to 10 carbon atoms and hydrogen atom, the former is preferable since it provides chemically more stable compounds.

By selecting suitable u and $R_2$ in combination, various side chain alkynyl groups expressed by the formula (20) can be obtained. Their preferable examples include 2-propynyl, 2-butynyl, 3-butynyl, 2-pentynyl, 3-pentynyl, 4-pentynyl, 2-hexynyl, 3-hexynyl, 4-hexynyl, 5-hexynyl, 2-heptynyl, 3-heptynyl, 4-heptynyl, 5-heptynyl, 6-heptynyl, 2-octynyl, 3-octynyl, 4-octynyl, 5-octynyl, 6-octynyl, 7-octynyl, 3-nonynyl, 3-decynyl, and 3-pentadecynyl. As more preferable groups, 2-propynyl, 2-butynyl, 3-butynyl, 2-pentynyl, 3-pentynyl, 4-pentynyl, 2-hexynyl, 3-hexynyl, 4-hexynyl, 5-hexynyl, 2-heptynyl, 3-heptynyl, 4-heptynyl, and 5-heptynyl can be mentioned.

In the liquid crystalline compounds of the present invention expressed by the general formula (1), each of the elements which form the compounds may be its isotope. This is because even when the compounds comprise an isotope, properties of liquid crystal compositions to be obtained are not noticeably changed and the same or similar effects to those when the isotope is not comprised in the compounds can be obtained.

Liquid crystalline compounds of the present invention expressed by the general formula (1) have a remarkably high Δn compared with conventional compounds and a good miscibility with other liquid crystalline compounds or liquid crystal compositions. Besides, liquid crystal compositions prepared by using the compound of the present invention exhibit such an effect that the compositions do not lose a nematic phase even at a low temperature (for example, at −20° C. required from their practical use).

Further, since the compounds of the present invention have a low viscosity, they do not increase the viscosity of liquid crystal compositions to be obtained even when they are used, as component of the compositions, in a large amount. Also, the compounds of the present invention are low in dependence of their viscosity on temperature, particularly at a region of low temperatures. Accordingly, liquid crystal compositions having a high response speed can be produced from the liquid crystalline compounds of the present invention.

Still further, since the compounds of the present invention are chemically stable, it is possible to maintain the specific resistance and voltage holding ratio of liquid crystal compositions at a very high level by using the compound. Also, since the compounds have a high stability against external factors such as ultraviolet rays and heat, the compounds are highly excellent as component of liquid crystal compositions actually used.

As discussed above, the liquid crystalline compounds of the present invention expressed by the general formula (1) have excellent properties, specifically a good miscibility with other liquid crystalline compounds in addition to a remarkably high Δn. These properties are supposedly imparted by such a specific structure in which compounds have, as a side chain, an alkynyl group expressed by the formula (20), namely, a composite group having therein triple bond (—C≡C—), and an alkylene group which is linked to the triple bond and a ring in the principal skelton at its right hand side and left hand side, respectively.

As liquid crystalline compounds having such alkynyl group as expressed by the formula (20) as a part of skelton, compounds which are indicated by such an expression that any methylene group in a side chain may be replaced by —C≡C— or compounds which have a terminal alkyne such as —CH$_2$—C≡CH are known to some extent. However, as to the former, disclosure of compounds is not sufficient as to enable any person skilled in the art to make and use the compounds without involving extensive experimentation. The latter compounds are concerned with insecticides or herbicides and thus they do not have any relations to liquid crystalline compounds in the technical field of the present invention.

While the liquid crystalline compounds of the present invention are preferable as component of liquid crystal compositions for STN in particular, the compounds are also suitable as component of liquid crystal compositions for such other uses as TN, guest-host mode, polymer dispersed liquid crystal display device, dynamic scattering mode, and active matrix mode. The compounds are also useful as component of ferroelectric liquid crystal composition, or antiferroelectric liquid crystal compositions.

Liquid crystal compositions provided by the present invention comprise, as a first component, at least one liquid crystalline compound expressed by the general formula (1).

In order to exhibit expected properties of liquid crystal compositions, the content of the compounds is necessary to be 0.1 to 99.9% by weight based on the amount of the liquid crystal composition, and the content is preferably 1 to 50% by weight and more desirably 3 to 20% by weight based on the amount of the liquid crystal composition.

While liquid crystal compositions of the present invention may comprise only the first component described above, the compositions can independently comprise, as a second component, at least one compound selected from the group of the compounds expressed by any one of the general formulas (2), (3), and (4) (hereinafter referred to as second A component), or at least one compound selected from the group consisting of the compounds expressed by the general formula (5) or (6) (hereinafter referred to as second B component), and comprise, as a third component, at least one compound selected from the group consisting of the compounds expressed by any one of the general formulas (7), (8), and (9) in addition to the first component. Further, the liquid crystal compositions may comprise, as a still further component, an optically active compound; and a known compound for the purpose of adjusting threshold voltage, temperature range of liquid crystal phase, Δε, Δn, and viscosity.

Among the second A component, the compounds expressed by any one of the following formulas (2-1) to (2-9) can be mentioned as preferable examples of the compounds included in the general formula (2). Also, as preferable examples of the compounds included in the general formula (3), the compounds expressed by any one of the following formulas (3-1) to (3-69); and as preferable examples of the compounds included in the general formula (4), the compounds expressed by any one of the following formulas (4-1) to (4-24) can be mentioned, respectively.

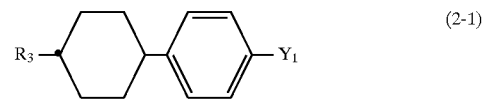

(2-1)

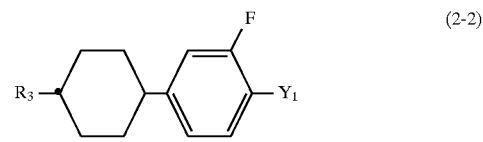

(2-2)

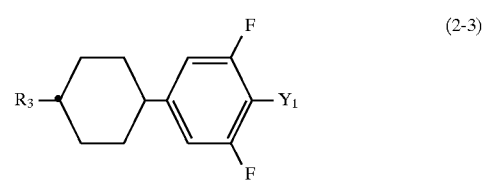

(2-3)

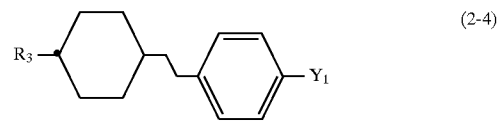

(2-4)

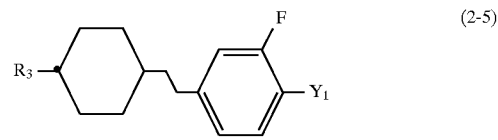

(2-5)

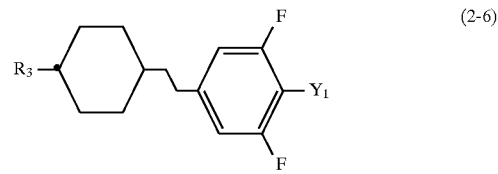

(2-6)

-continued
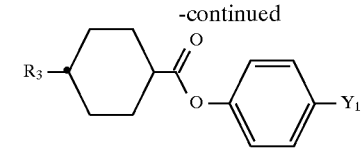 (2-7)
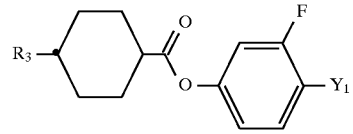 (2-8)
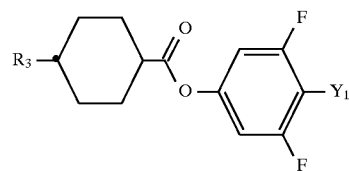 (2-9)
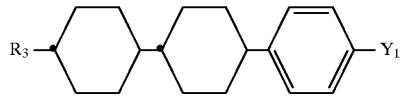 (3-1)
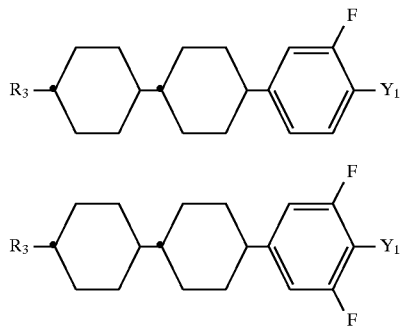 (3-2)
(3-3)
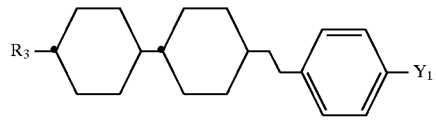 (3-4)
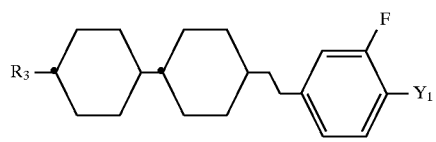 (3-5)
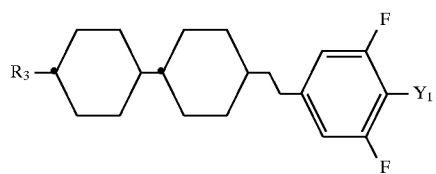 (3-6)
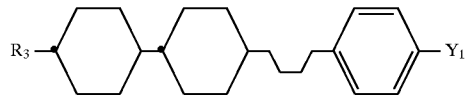 (3-7)
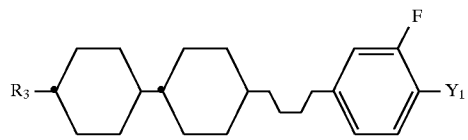 (3-8)
-continued
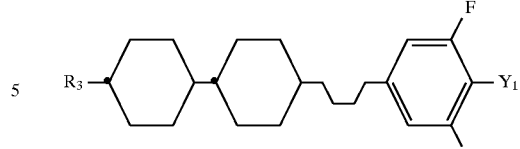 (3-9)
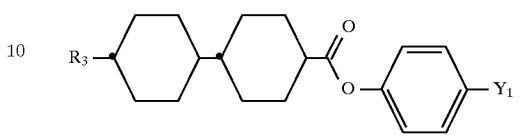 (3-10)
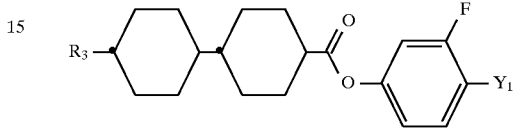 (3-11)
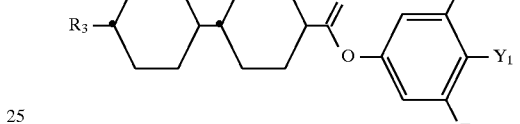 (3-12)
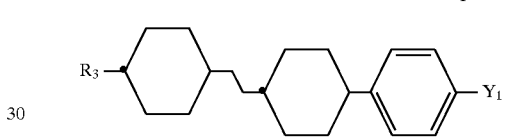 (3-13)
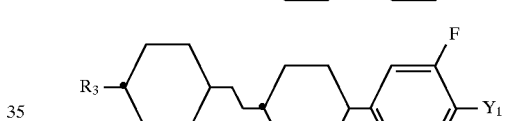 (3-14)
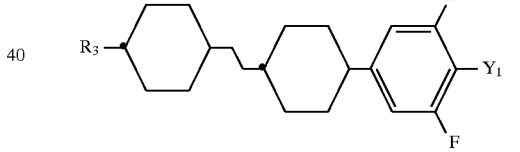 (3-15)
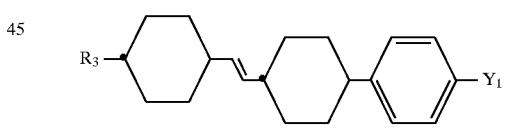 (3-16)
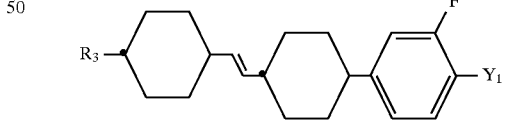 (3-17)
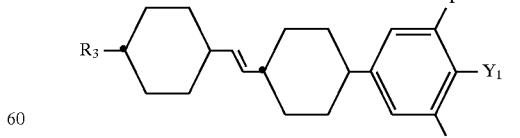 (3-18)
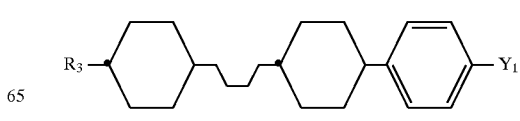 (3-19)

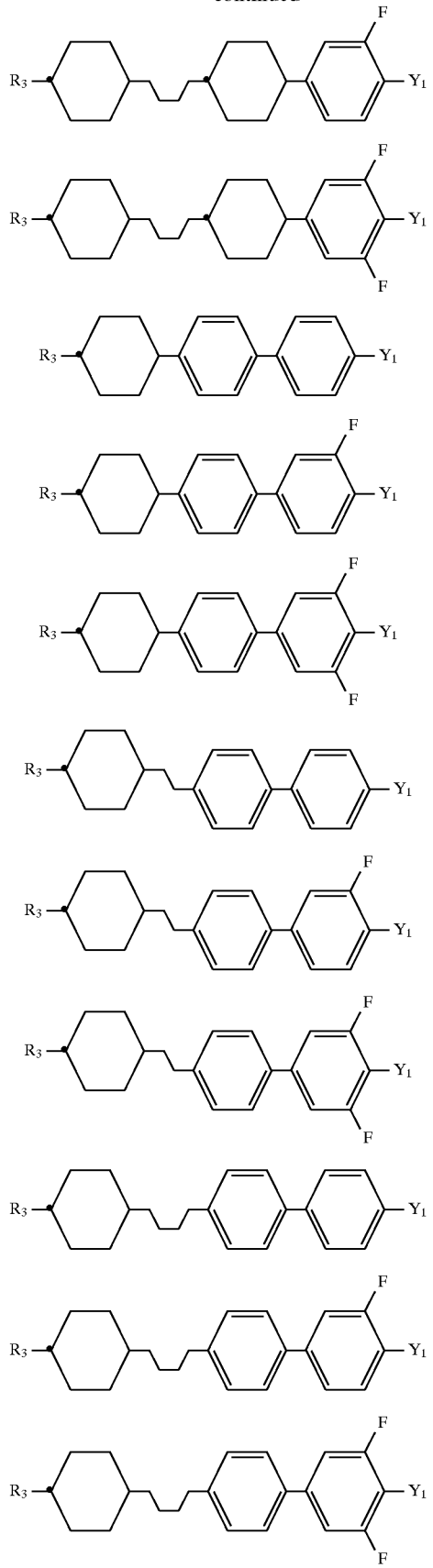

-continued
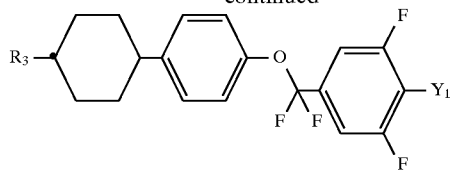 (3-42)
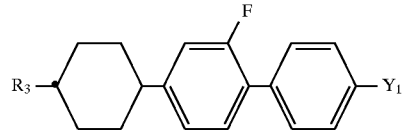 (3-43)
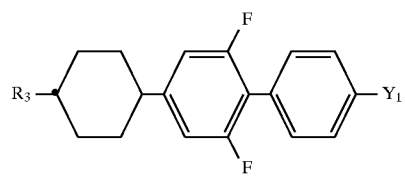 (3-44)
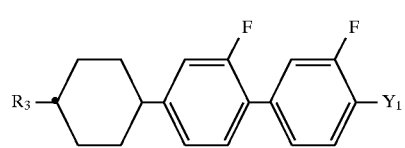 (3-45)
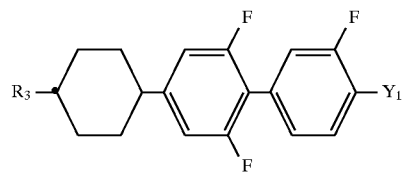 (3-46)
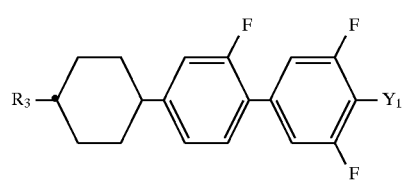 (3-47)
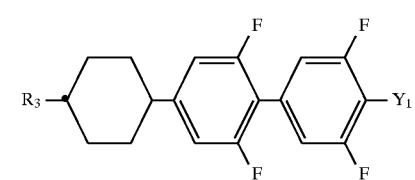 (3-48)
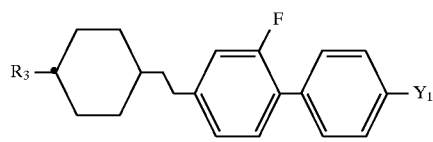 (3-49)
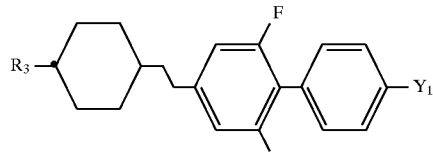 (3-50)
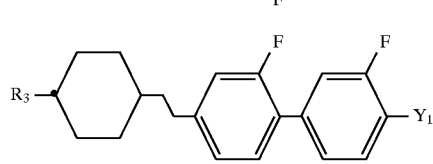 (3-51)
-continued
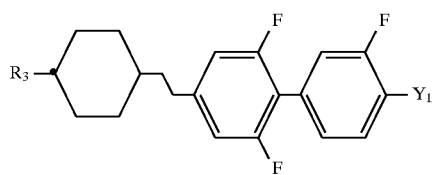 (3-52)
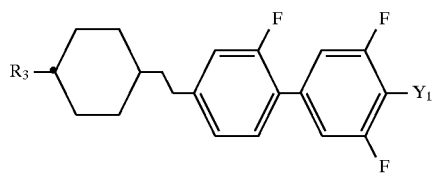 (3-53)
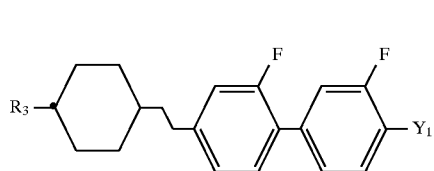 (3-54)
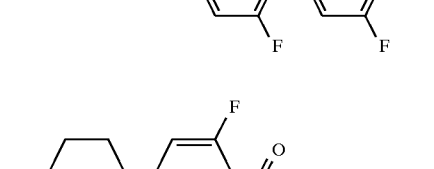 (3-55)
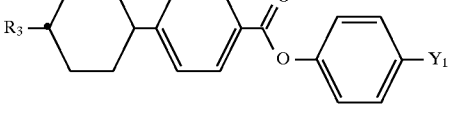 (3-56)
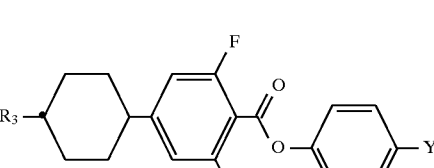 (3-57)
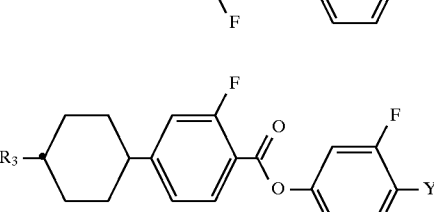 (3-58)
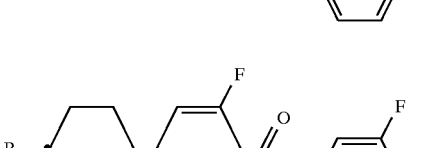 (3-59)

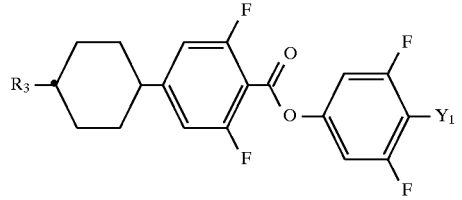 (3-60)
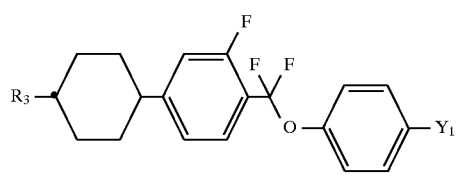 (3-61)
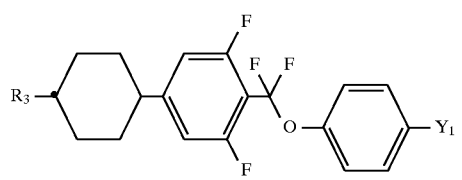 (3-62)
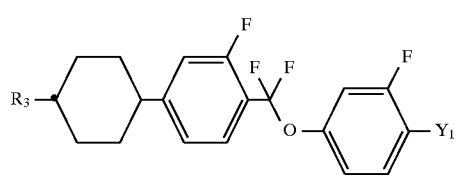 (3-63)
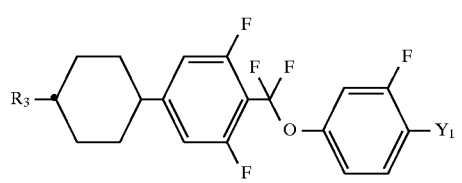 (3-64)
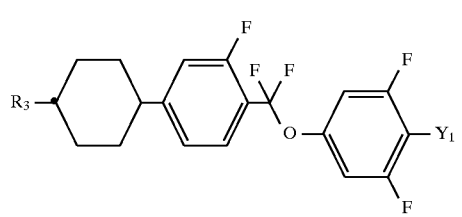 (3-65)
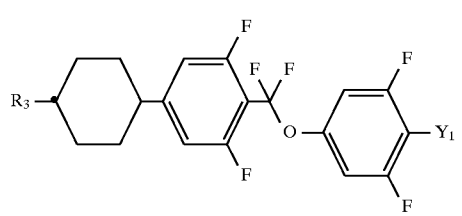 (3-66)
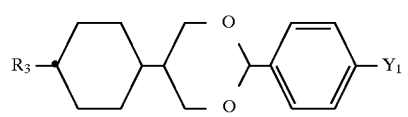 (3-67)
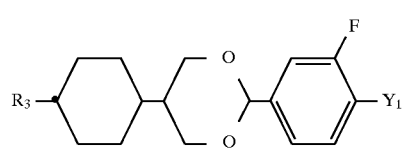 (3-68)
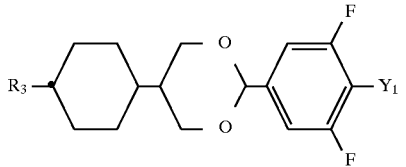 (3-69)
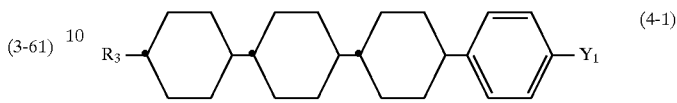 (4-1)
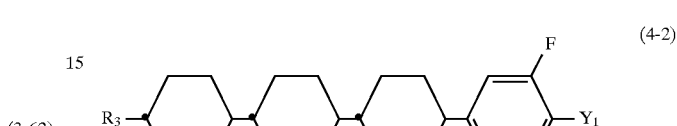 (4-2)
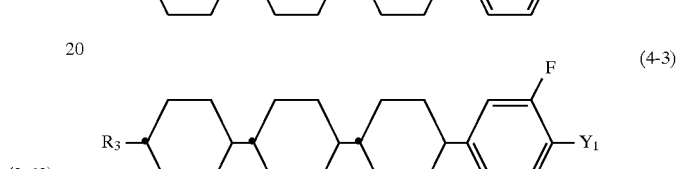 (4-3)
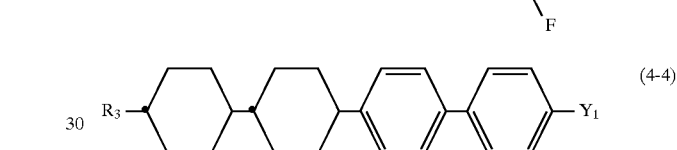 (4-4)
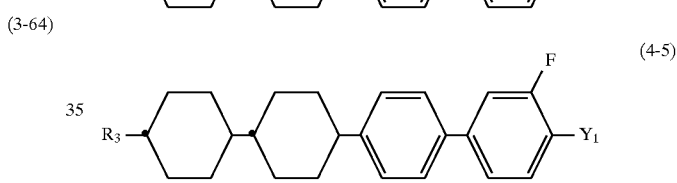 (4-5)
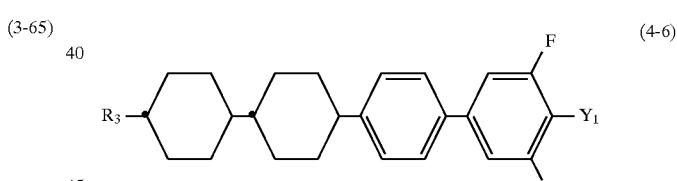 (4-6)
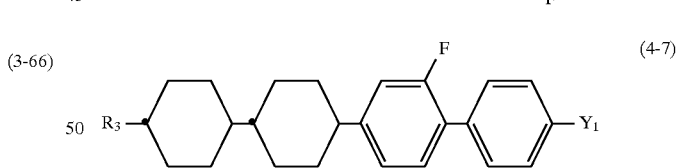 (4-7)
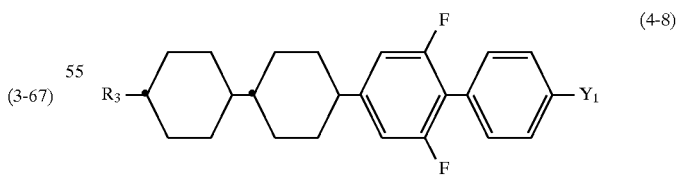 (4-8)
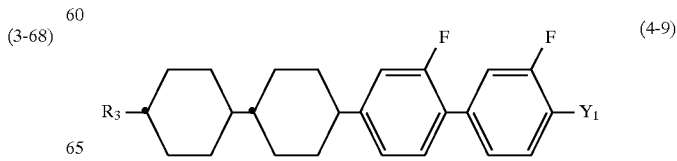 (4-9)

-continued

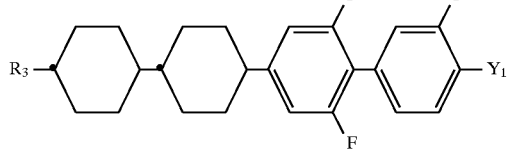 (4-10)

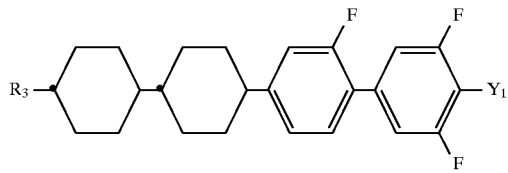 (4-11)

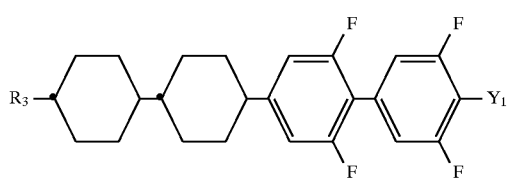 (4-12)

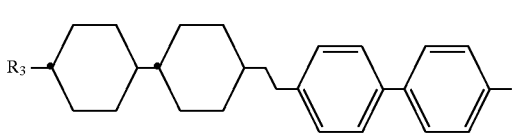 (4-13)

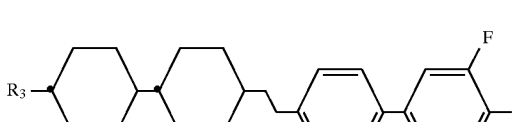 (4-14)

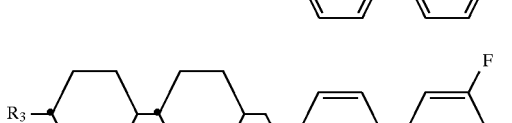 (4-15)

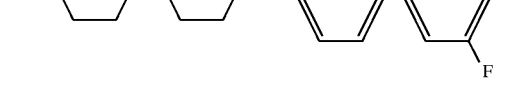 (4-16)

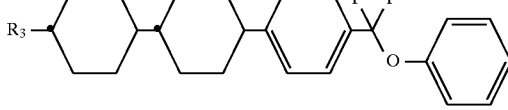 (4-17)

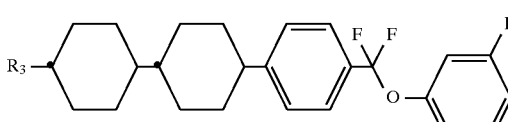 (4-18)

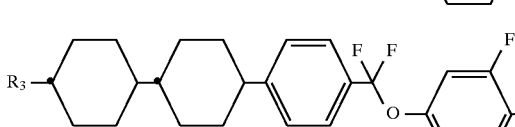 (4-19)

-continued

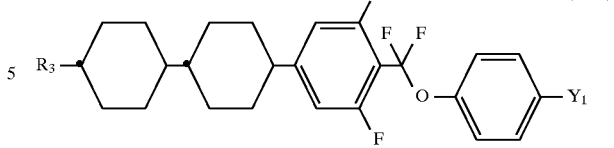 (4-20)

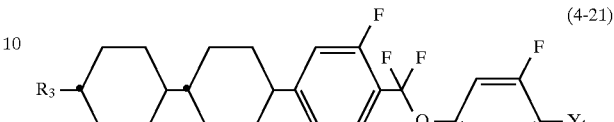 (4-21)

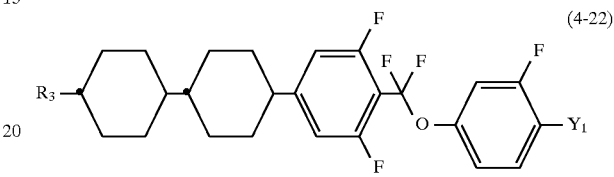 (4-22)

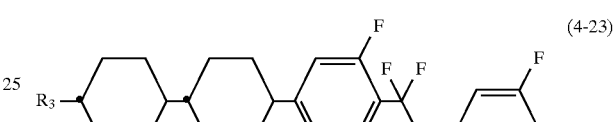 (4-23)

 (4-24)

wherein $R_3$ and $Y_1$ have the same meaning as those described above.

Since compounds expressed by any one of the general formulas (2) to (4) have a positive $\Delta\epsilon$, are excellent in thermal stability and chemical stability, and have a high voltage holding ratio (high specific resistance), they are indispensable when liquid crystal compositions for active matrix mode (represented by TFT) of which a high reliability is required are produced.

Amount of the compounds to be used is suitably 1 to 99% by weight based on the total amount of the liquid crystal composition when liquid crystal compositions for TFT are produced, and the amount is preferably 10 to 97% by weight and more desirably 40 to 95% by weight. At that time, liquid crystal compositions may comprise a compound expressed by any one of the general formulas (7) to (9).

Compounds expressed by any one of the general formulas (2) to (4) described above can be used even when liquid crystal compositions for STN or TN are produced. However, since the effect of the compounds on reducing threshold voltage of liquid crystal compositions is small, the amount of the compounds to be used is preferably less than 50% by weight based on the total amount of the liquid crystal composition.

Among the second B component described above, the compounds expressed by any one of the following formulas (5-1) to (5-40) can be mentioned as preferable examples of the compounds included in the general formula (5); and the compounds expressed by any one of the following formulas (6-1) to (6-3) can be mentioned as preferable examples of the compounds included in the general formula (6).
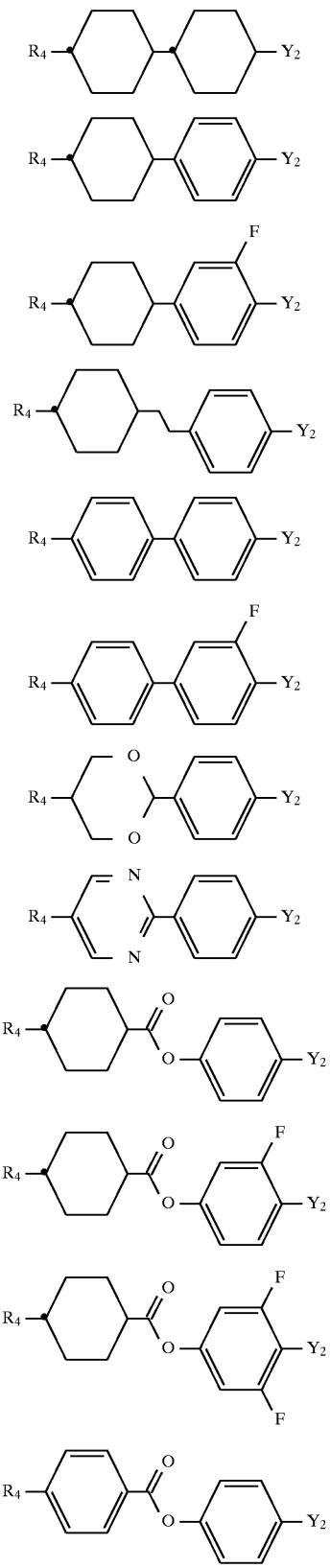
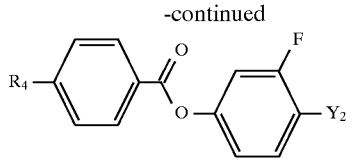
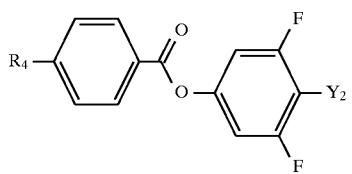
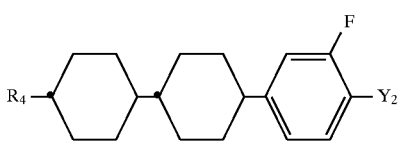
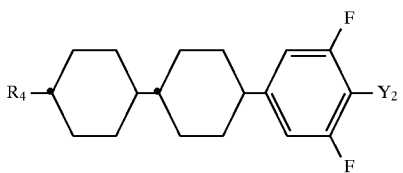
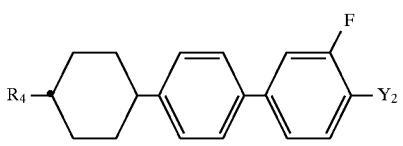
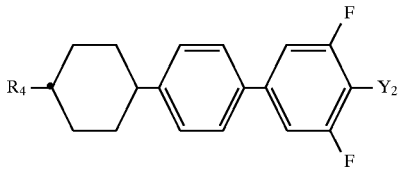
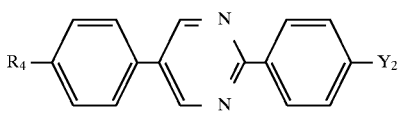
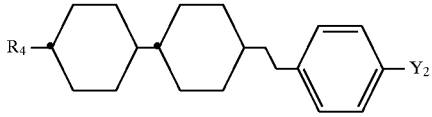

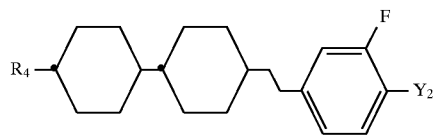 (5-24)

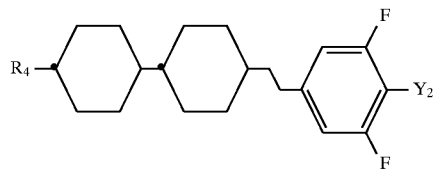 (5-25)

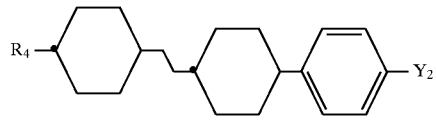 (5-26)

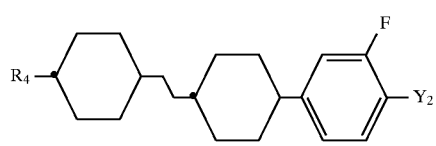 (5-27)

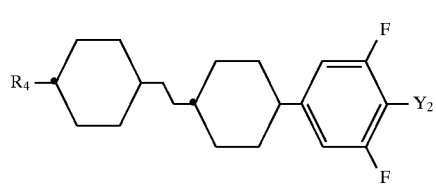 (5-28)

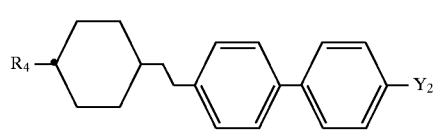 (5-29)

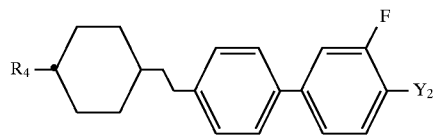 (5-30)

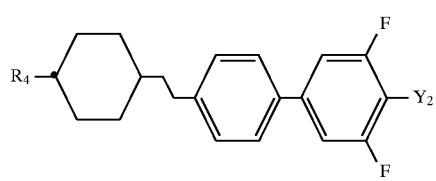 (5-31)

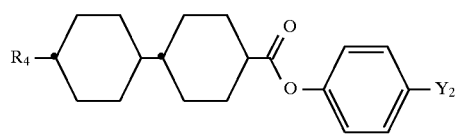 (5-32)

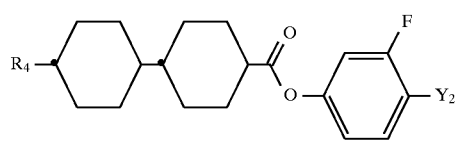 (5-33)

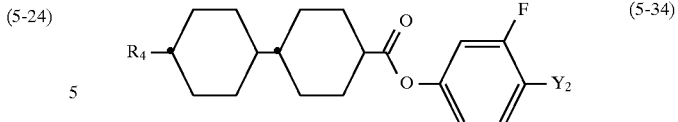 (5-34)

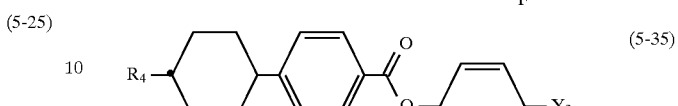 (5-35)

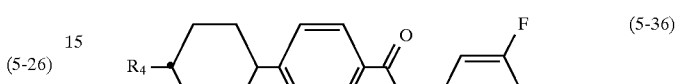 (5-36)

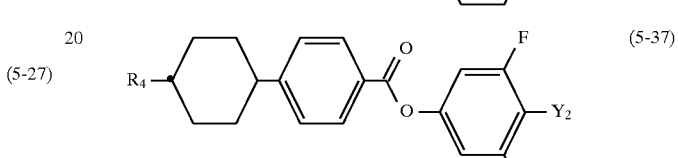 (5-37)

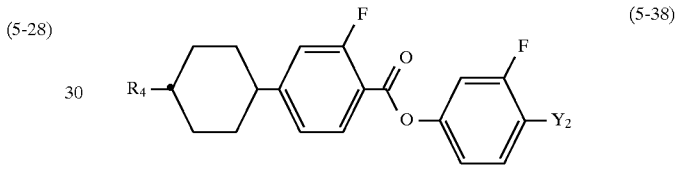 (5-38)

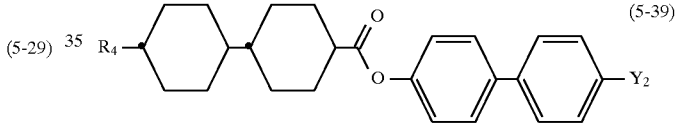 (5-39)

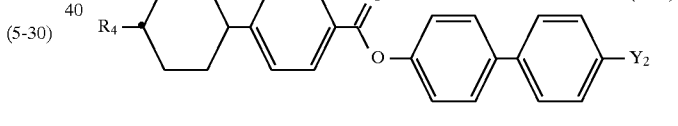 (5-40)

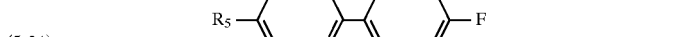 (6-1)

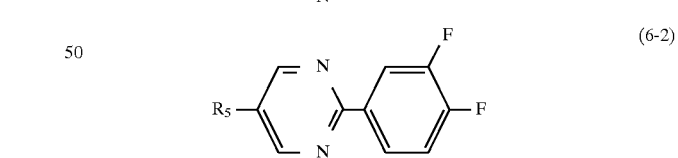 (6-2)

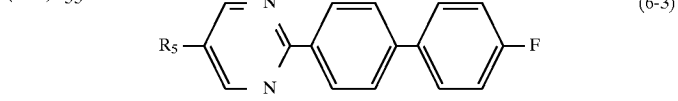 (6-3)

wherein $R_4$, $R_5$, and $Y_2$ have the same meaning as those described above.

Since compounds expressed by the general formula (5) or (6) have a positive high Δε value, they are used for the purpose of reducing threshold voltage of liquid crystal compositions. Also, they are used for the purpose of improving steepness of threshold voltage of liquid crystal compositions for STN or TN, including for the purpose of adjusting Δn and widening a nematic range such as raising clearing point. Accordingly, they are indispensable when liquid crystal compositions for STN or TN are produced.

With increase in the amount of the compounds to be used, threshold voltage of liquid crystal compositions can be reduced. On the other hand, however, viscosity of liquid crystal compositions is increased when the amount of the compounds is increased. Accordingly, so far as the viscosity satisfies the properties required of liquid crystal compositions, the amount of the compounds to be used is advantageously as much as possible from the viewpoint of driving liquid crystal display devices at a low voltage.

From these circumstances, the amount of the compounds to be used is suitably in the range of 0.1 to 99.9% by weight based on the total amount of the liquid crystal composition when liquid crystal compositions for STN or TN are produced, and the amount is preferably 10 to 97% by weight and more desirably 40 to 95% by weight.

Among the third component described above, the compounds expressed by any one of the following formulas (7-1) to (7-11) can be mentioned as preferable examples of the compounds included in the general formula (7). Also, as preferable examples of the compounds included in the general formula (8), the compounds expressed by any one of the formulas (8-1) to (8-18); and as preferable compounds included in the general formula (9), the compounds expressed by any one of the following formulas (9-1) to (9-6) can be mentioned, respectively.

 (7-1)

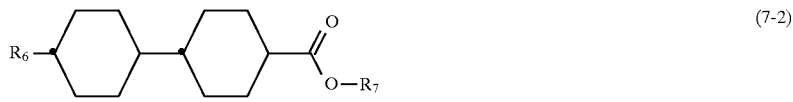 (7-2)

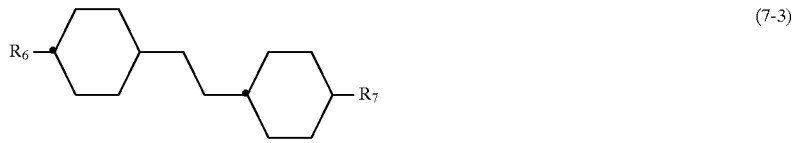 (7-3)

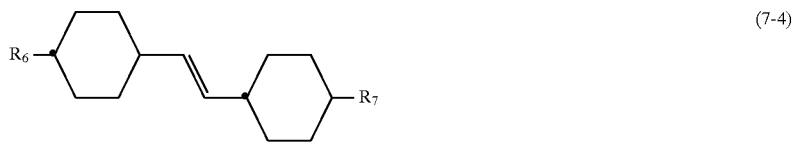 (7-4)

 (7-5)

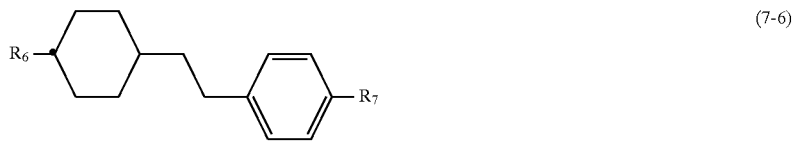 (7-6)

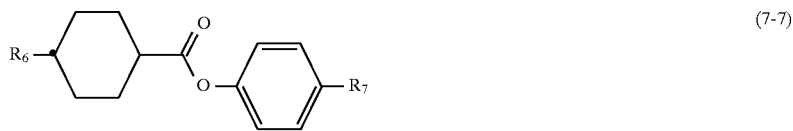 (7-7)

 (7-8)

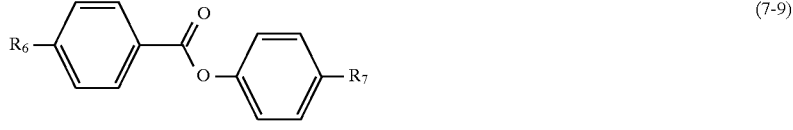 (7-9)

 (7-10)

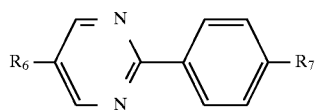 (7-11)
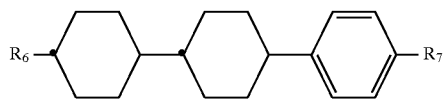 (8-1)
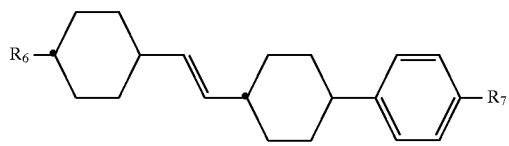 (8-2)
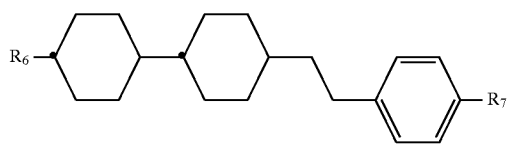 (8-3)
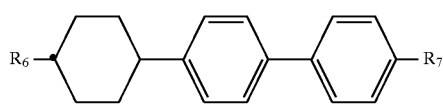 (8-4)
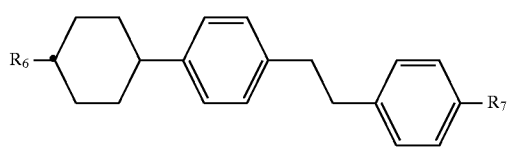 (8-5)
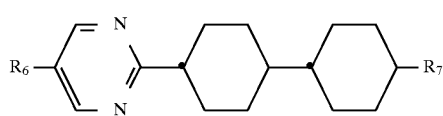 (8-6)
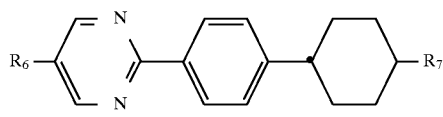 (8-7)
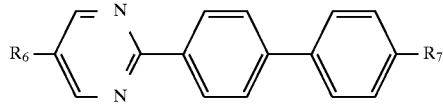 (8-8)
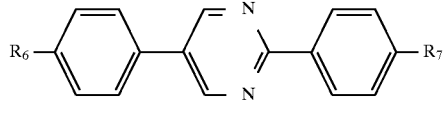 (8-9)
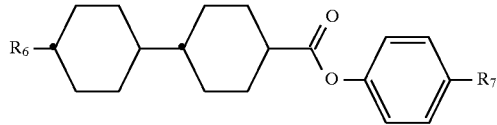 (8-10)
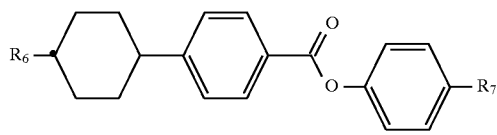 (8-11)

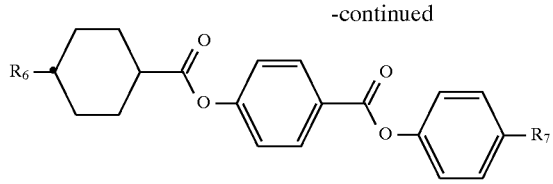 (8-12)
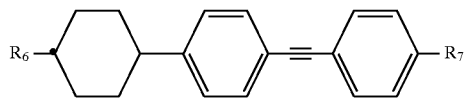 (8-13)
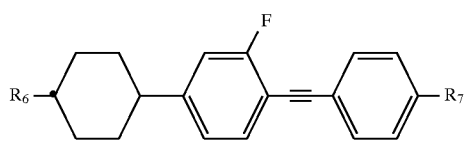 (8-14)
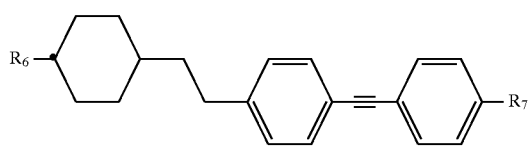 (8-15)
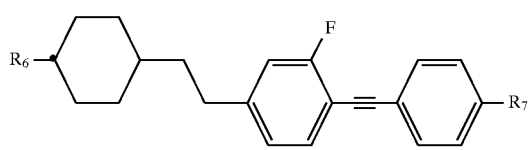 (8-16)
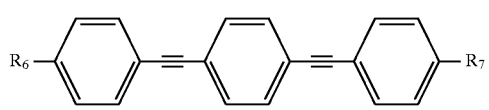 (8-17)
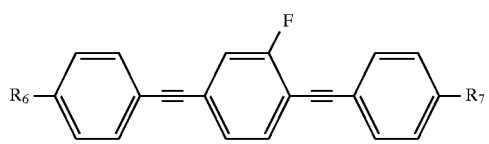 (8-18)
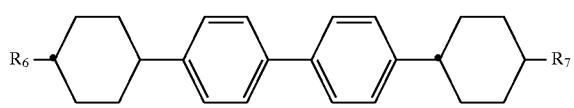 (9-1)
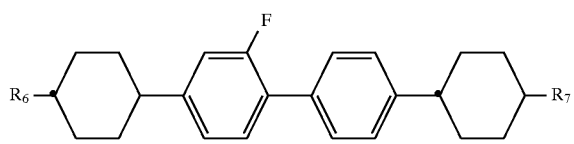 (9-2)
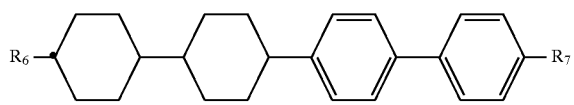 (9-3)
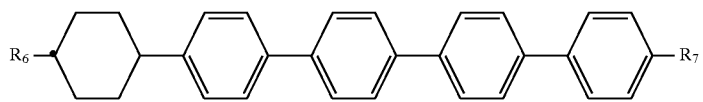 (9-4)
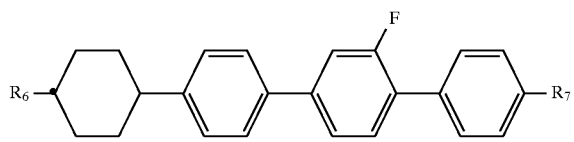 (9-5)

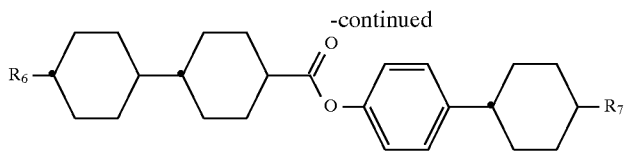

(9-6)

wherein $R_6$ and $R_7$ have the same meaning as those described above.

Compounds expressed by any one of the general formulas (7) to (9) have an absolute value of $\Delta\epsilon$ of about 0, and are almost neutral. Among them, compounds expressed by the general formula (7) can be used mainly for the purpose of adjusting viscosity or $\Delta$n of liquid crystal compositions, and compounds expressed by the general formula (8) or (9) are used for the purpose of widening a nematic range such as raising clearing point and adjusting $\Delta$n of liquid crystal compositions.

With increase in the amount of the compounds to be used, threshold voltage of liquid crystal compositions is raised. On the other hand, however, viscosity of liquid crystal compositions is reduced when the amount of the compounds is increased. Accordingly, so far as the threshold voltage satisfies the properties required of liquid crystal compositions, the amount of the compounds to be used is preferably as much as possible.

From these circumstances, the amount of the compounds to be used is suitably less than 40% by weight based on the total amount of the liquid crystal composition when liquid crystal compositions for TFT are produced, and the amount is preferably less than 35% by weight. On the other hand, when liquid crystal compositions for STN or TN are produced, the amount of the compounds to be used is suitably less than 70% by weight and preferably less than 60% by weight.

Among other components described above, the optically active compound is usually added to liquid crystal compositions for the purpose of inducing a helical structure of liquid crystals, adjusting a required twist angle, and thus avoiding a reverse twist, excluding, for instance, a case in which liquid crystal compositions for OCB (optically compensated birefringence) mode are produced.

So far as the purposes described above are achieved, the optically active compound is selected from a wide range of known compounds, and compounds expressed by any one of the following formulas (Op-1) to (Op-8) can be mentioned as preferable optically active compounds.

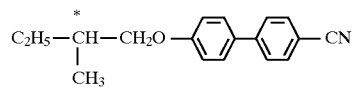

(Op-1)

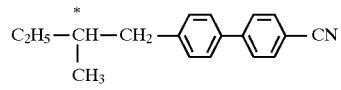

(Op-2)

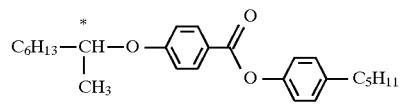

(Op-3)

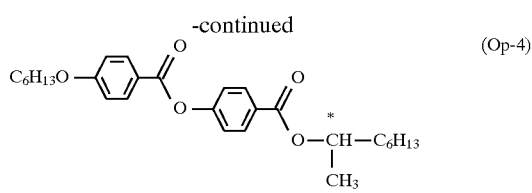

(Op-4)

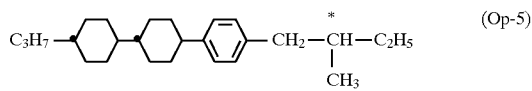

(Op-5)

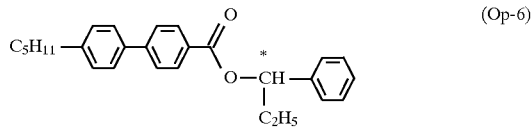

(Op-6)

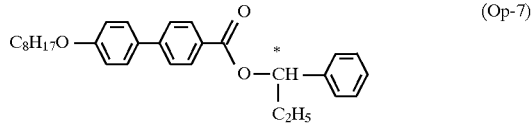

(Op-7)

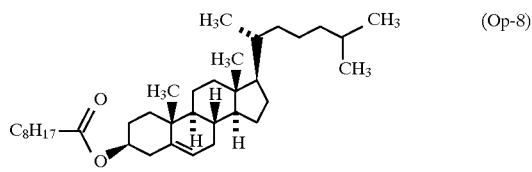

(Op-8)

By adding a suitable amount of the optically active compound in liquid crystal compositions, pitch length of the twist of liquid crystals in compositions is adjusted. It is preferable to adjust the twist pitch length to 40 to 200 $\mu$m for liquid crystal compositions for TFT or TN, 6 to 20 $\mu$m for STN, and 1.5 to 4 $\mu$m for bistable TN mode, respectively.

Further, two or more kind of optically active compounds may be used in combination at that time for the purpose of optimizing the dependency of pitch length on temperature.

Liquid crystal compositions provided according to the present invention are generally produced by a method which is conventional by itself. For instance, the compositions are produced by a method in which various components are dissolved in each other at a high temperature.

When a dichroic dye such as merocyanine type, styryl type, azo type, azomethine type, azoxy type, quinophthalone type, anthraquinone type, or tetrazine type is added at the time of production of liquid crystal compositions, the compositions can be used as liquid crystal compositions for guest-host (GH) mode. Liquid crystal compositions of the present invention can be used as compositions for an electrically controlled birefringence (ECB) mode or a dynamic scattering (DS) mode, including as liquid crystal compositions for polymer dispersion liquid crystal display devices (PDLCDs) represented by a NCAP which is prepared by the microencapsulation of a nematic liquid crystal or represented by polymer network liquid crystal display devices (PNLCDs) which are prepared by forming a polymer of three-dimensional reticulated structure in a liquid crystal.

Liquid crystalline compounds of the present invention expressed by the general formula (1) can readily be produced by using procedures described in known literatures, for example, Organic Synthesis, Organic Reactions, and "Jikken Kagaku Kouza (Course of Chemical Experiment) (Maruzen) in a suitable combination.

Namely, liquid crystalline compounds of the present invention expressed by the general formula (1) can be obtained by reacting a 1-hydroxyalkyne (13) with phosphorous tribromide (cf. a method described in J. Am. Chem. Soc., 71, 1292 (1949)) or with triphenylphosphine dibromide (cf. a method described in Org. Synth., V, 249 (1973)) to form a bromide (14), converting -the bromide (14) into a Grignard reagent (15), and then reacting the Grignard reagent (15) with an iodide or bromide (16) (cf. a method described in J. Chem. Soc. Chem. Commun., 144 (1972) or J. Am. Chem. Soc., 94, 4374 (1972)) in the presence of a catalyst.

In this connection, a starting material 1-hydroxyalkyne (13) mentioned above can be produced by a method described in copending senior Japanese Patent Application No. Hei 8-047947 filed by the present applicants in which a 1-alkyne is reacted with n-BuLi and then reacted with a cyclic ether to cause a ring opening reaction.

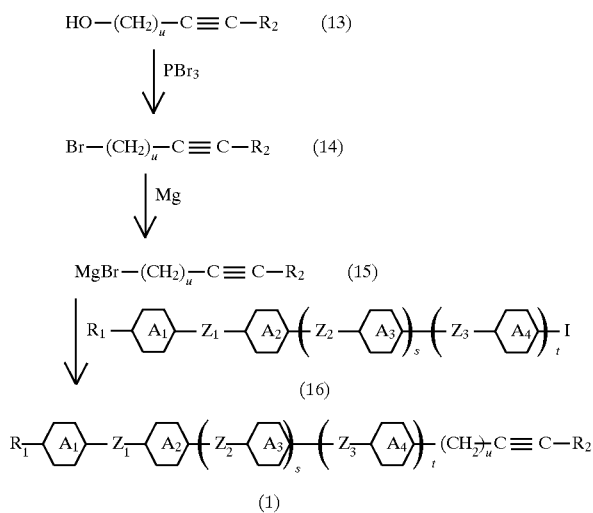

Among the liquid crystal compositions of the present invention expressed by the general formula (1), compounds in which the ring directly bonding to an alkynyl group expressed by the formula (20) described above is particularly 1,4-phenylene or 1,4-phenylene substituted with a halogen atom can also be produced by the following reaction path:

That is, the compounds can be produced by using an iodide (17) and a 4-alkynyl-iodobenzene (18) unsubstituted or substituted with a halogen atom, and subjecting one of them with the other, which was converted into a Grignard reagent or lithium reagent, to a cross coupling reaction.

Compound (18) mentioned above can be obtained by a method described in Japanese Patent Application No. Hei 8-047947 in which a 1-iodoalkyne obtained by iodizing the 1-hydroxyalkyne (13) mentioned above, and an iodized benzene derivative are subjected to a cross coupling reaction.

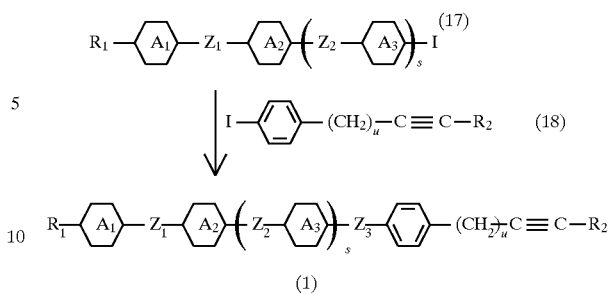

Now, the present invention will be described in more detail with reference to Examples. However, it should be understood that the present invention is by no means restricted by such specific Examples.

In the Examples, C indicates a crystal, S does a smectic phase, N does a nematic phase, and I indicates a phase of an isotropic liquid.

EXAMPLE 1

Preparation of 4'-(2-propenyl)-3-fluoro-4-(3-pentyne-1-yl)biphenyl (Compound expressed by the general formula (1) wherein $R_1$ represents 2-propenyl group, $R_2$ represents methyl group, s and t are 0, u is 2, ring $A_1$ represents 1,4-phenylene, ring $A_2$ represents 3-fluoro-1,4-phenylene, and $Z_1$ represents a covalent bond; Compound No. 1)

To a mixture comprising 4-bromo-iodobenzene (350 mmol), dilithium copper tetrachloride (15 mmol), and 500 ml of diethyl ether, was added dropwise 1M solution of allyl magnesium bromide on the market (corresponding to 300 mmol) in diethyl ether at a temperature lower than 10° C. in 2 hours. The solvent was removed under a reduced pressure and the residue was distilled under a reduced pressure to obtain a crude oily 4-allyl-bromobenzene. This product was rectified with an Oldershow column (number of theoretical plates is 10) to obtain 4-allyl-bromobenzene (127 mmol) as the distillate at 130°–134° C./9 mmHg.

To a mixture comprising sufficiently dried metal magnesium (120 mmol) and 30 ml of tetrahydrofuran (hereinafter referred to as THF), was gradually added a solution of 120 mmol of the 4-allyl-bromobenzene in 200 ml of THF to prepare a Grignard reagent. To this reagent was added dropwise a solution of trimethyl borate (120 mmol) in 100 ml of THF at a temperature not exceeding −65° C., stirred for a whole day and night. Subsequently, the mixture was kept at 0° C., 200 ml of 10% hydrochloric acid was gradually added thereto at the same temperature, and then the reaction mixture was stirred for 30 min. The mixture thus obtained was extracted twice with 500 ml of diethyl ether, the organic layer was washed with a saturated brine solution, and then the solvent was removed under a reduced pressure. The residue was sufficiently washed with 500 ml of heptane and then dried to obtain 4-allylphenyl boric acid (79 mmol).

A mixture of 10 mmol of the 4-allylphenyl boric acid, 0.1 g of 50% hydropalladium carbon, anhydrous potassium carbonate (20 mmol), 3-fluoro-4-(3-pentyne-1-yl)-iodobenzene (67 mmol) prepared according to a method described in Japanese Patent Application No. Hei 8-047947, 14 ml of toluene, 14 ml of ethanol, and 0.7 ml of water was heated to reflux for 4 hours. The reaction mixture was cooled, sufficiently washed with water, and then dried over anhydrous magnesium sulfate. The solvent was removed under a reduced pressure, the residue was purified by subjecting to silica gel column chromatography (eluent:

toluene) and then subjecting to recrystallization (solvent: ethanol) to obtain the subject compound (39 mmol). Various spectral data of the compound well supported its structure.

EXAMPLE 2

Preparation of 4'-(4-ethylcyclohexyl)-2'-fluoro-4-(3-pentyne-1-yl)biphenyl (Compound expressed by the general formula (1) wherein $R_1$ represents ethyl group, $R_2$ represents methyl group, s is 1, t is 0, u is 2, ring $A_1$ represents 1,4-cyclohexylene, ring $A_2$ represents 3-fluoro-1,4-phenylene, ring $A_3$ represents 1,4-phenylene, and both $Z_1$ and $Z_2$ represent a covalent bond; Compound No. 2)

Mixture of 2-fluoro-4-(4-ethylcyclohexyl)benzene (50 mmol) and 95 ml of THF was cooled to a temperature lower than −70° C. To this mixture was added dropwise 1.6M solution of butyllithium (corresponding to 55 mmol) in hexane while keeping the same temperature in 1 hour, and stirred for 30 min as they were. Subsequently, 0.5M solution of zinc chloride (corresponding to 60 mmol) in THF was added dropwise while maintaining the same temperature to obtain a pale yellow homogeneous solution. To this solution were added in one breath tetrakistriphenyl phosphine palladium (0) (2.5 mmol) and 4-(3-pentyne-1-yl)-iodobenzene (50 mmol) prepared by a method described in Japanese Patent Application No. Hei 8-047947, heated to reflux for 3 hours, and then cooled.

To this reaction mixture was carefully added 50 ml of water, heptane (120 ml) was further added, and they were vigorously stirred. After allowed to settle, the separated organic layer was washed with a saturated brine solution, and then dried over anhydrous magnesium sulfate. The solvent was removed under a reduced pressure, and the residue thus obtained was purified by subjecting to silica gel column chromatography (eluent: heptane) and then to recrystallization (solvent: ethanol) to obtain the subject compound (13 mmol). Various spectral data of the compound well supported its structure.

EXAMPLE 3

Preparation of 4'-(4-(4-propylcyclohexyl)cyclohexyl)-4-(3-pentyne-1-yl)biphenyl (Compound expressed by the general formula (1) wherein $R_1$ represents propyl group, $R_2$ represents methyl group, s and t are 1, u is 2, ring $A_1$ and ring $A_2$ represent 1,4-cyclohexylene, ring $A_3$ and ring $A_4$ represent 1,4-phenylene, and all of $Z_1$, $Z_2$, and $Z_3$ represent a covalent bond; Compound No. 3)

To a mixture of sufficiently dried magnesium and 20 ml of THF was added dropwise a solution of 4-(3-pentyne-1-yl)-idodbenzene, prepared according to a method described in the Japanese Patent Application No. Hei 8-047947 mentioned above, in 80 ml of THF to prepare a homogeneous grey Grignard reagent. To this reagent was added a mixture comprising 4-(4-(4-propylcyclohexyl)cyclohexyl)-iodobenzene (95 mmol), bis(triphenylphosphine) palladium (II) dicloride (4 mmol), and 90 ml of THF, and heated to reflux for 2 hours.

From the reaction mixture, 100 ml of the solvent was removed under a reduced pressure, 150 ml of toluene and 200 ml of water were added to the residue, and they were sufficiently stirred. After allowed to settle, the separated organic layer was sufficiently washed with a saturated brine solution and then dried over anhydrous magnesium sulfate. The solvent was removed under a reduced pressure, and the residue was purified by subjecting to silica gel column chromatography (eluent: toluene/hexane mixed solvent) and then to recrystallization (solvent: heptane) to obtain the subject compound (28 mmol). Various spectral data of the compound well supported its structure.

Based on the procedures described in Examples 1 to 3, the following compounds, Compound Nos. 4 to 128 are prepared.

Among the data on properties of the compounds, Δε, Δn, η (viscosity) are shown as values obtained by extrapolation from the values of properties of the compositions obtained by mixing 15% by weight of each concerned compound with 85% by weight of liquid crystal composition B1 (Δε: 11.0, Δn: 0.137, η: 27.3 mPa·s) having the following chemical composition:

| | |
|---|---|
| 4-(4-propylcyclohexyl)benzonitrile | 24% by weight |
| 4-(4-pentylcyclohexyl)benzonitrile | 36% by weight |
| 4-(4-heptylcyclohexyl)benzonitrile | 25% by weight |
| 4-(4-pentylcyclohexyl)-4-cyanobiphenyl | 15% by weight |

| No. | | |
|---|---|---|
| 4 | 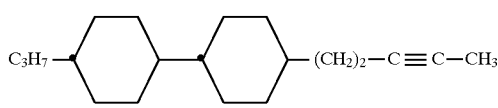 | C 34.0 N 75.5 I, Δε 9.8, Δn 0.129 |
| 5 | 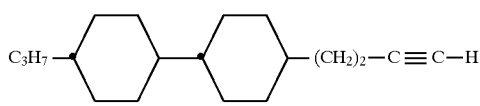 | C 38.5 N 58.5 I |
| 6 | 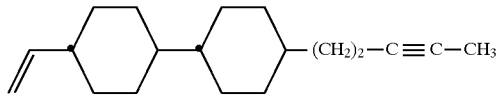 | |
| 7 | 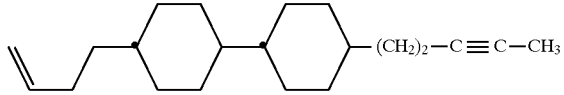 | |

-continued
| No. | |
|---|---|
| 8 | 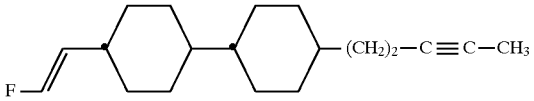 |
| 9 | 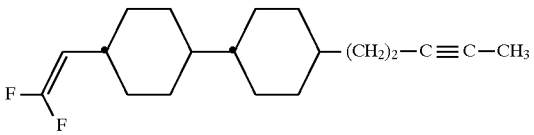 |
| 10 | 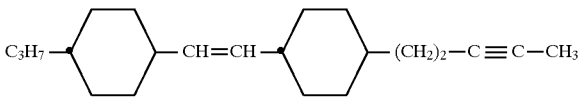 |
| 11 | 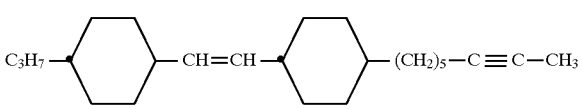 |
| 12 | 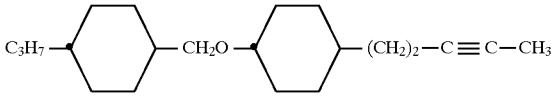 |
| 13 | 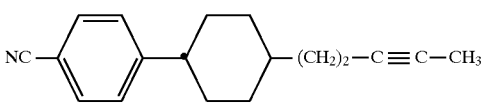 |
| 14 | 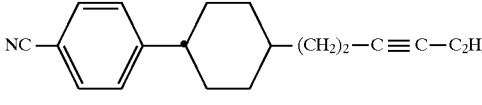 |
| 15 | 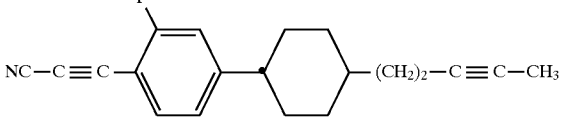 |
| 16 | 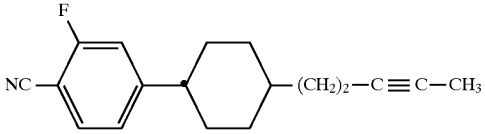 |
| 17 | 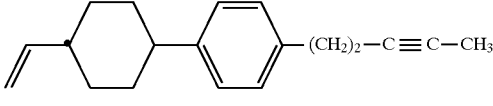 |
| 18 | 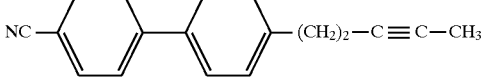 |
| 19 | 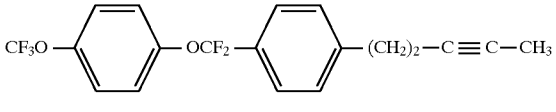 |
| 20 | 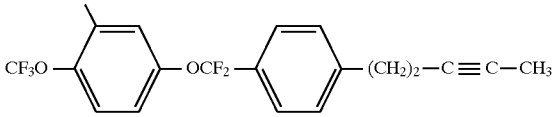 |

-continued
| No. | |
|---|---|
| 21 | 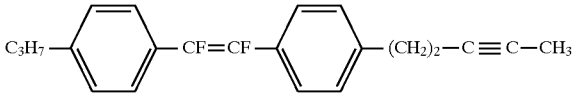 |
| 22 |  |
| 23 | 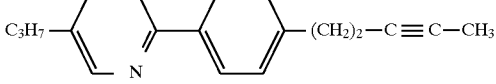 |
| 24 | 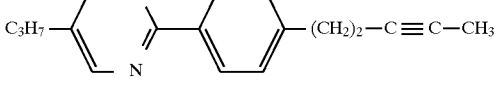 |
| 25 | 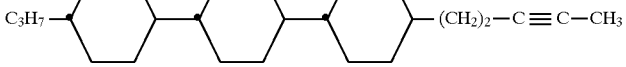 |
| 26 | 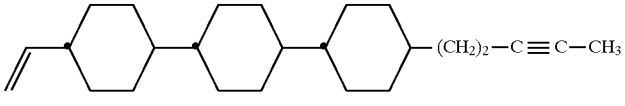 |
| 27 | 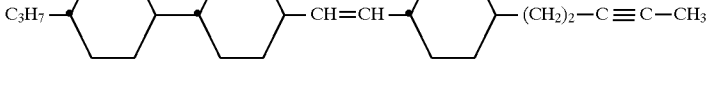 |
| 28 | 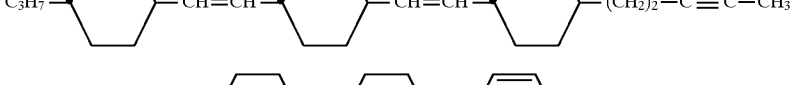 |
| 29 | 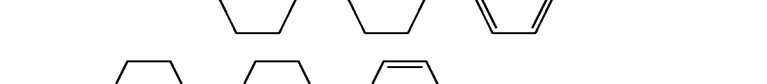 |
| 30 | 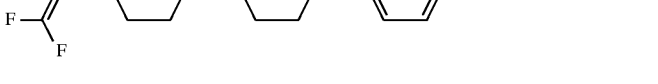 |
| 31 | 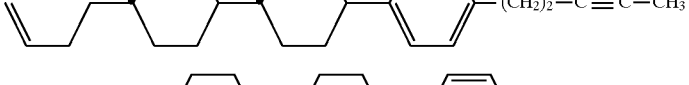 |
| 32 | 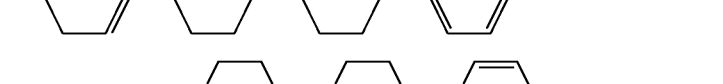 |
| 33 |  |
| 34 | 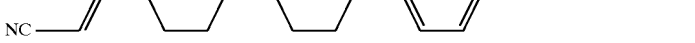 |

-continued
| No. | |
|---|---|
| 35 | 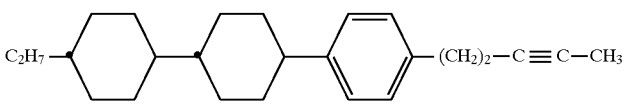 |
| 36 | 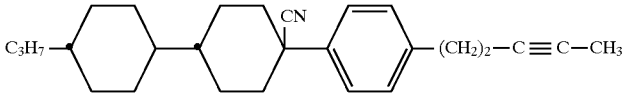 |
| 37 | 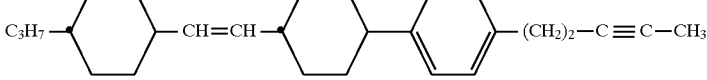 |
| 38 | 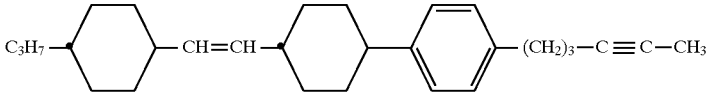 |
| 39 | 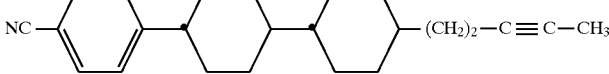 |
| 40 | 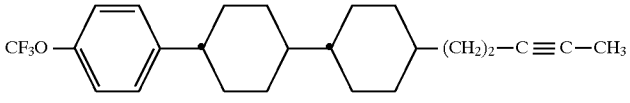 |
| 41 | 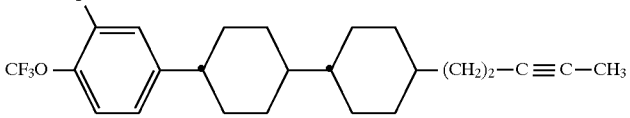 |
| 42 | 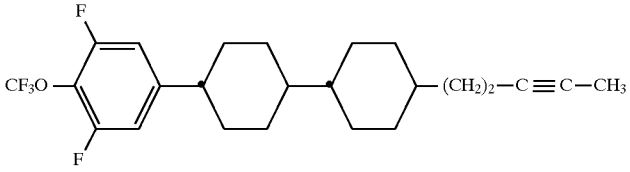 |
| 43 | 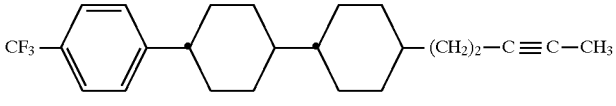 |
| 44 | 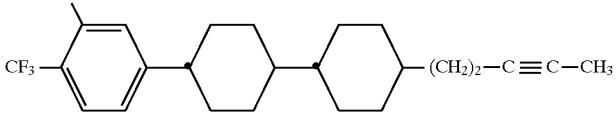 |
| 45 | 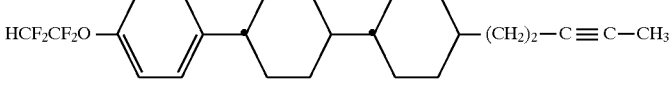 |
| 46 | 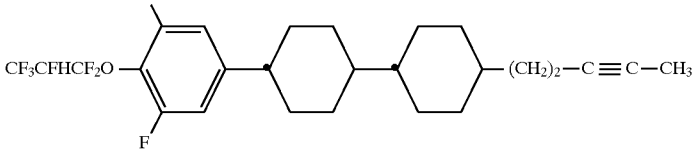 |

|No.| | |
|---|---|---|
|47|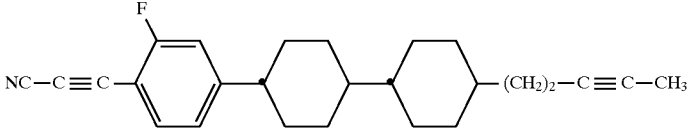| |
|48|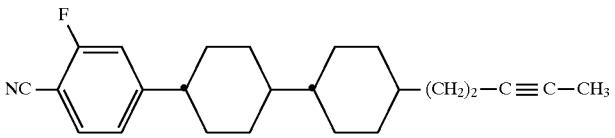| |
|49|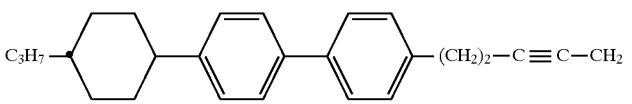| |
|50|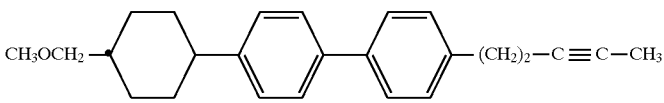| |
|51|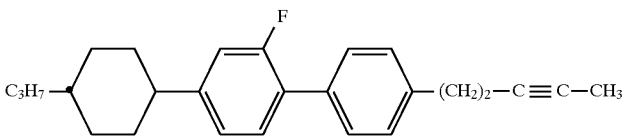| |
|52|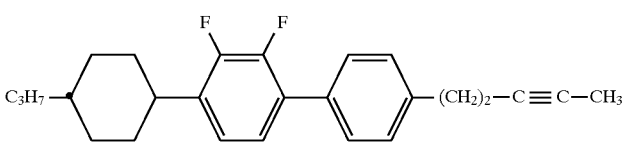| |
|53|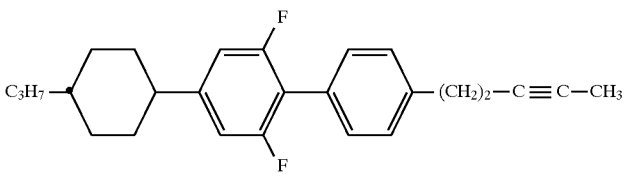| |
|54|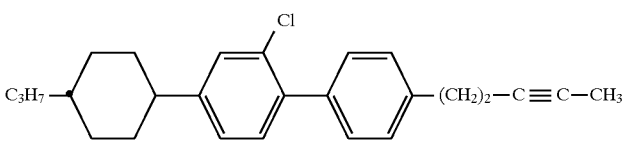| |
|55|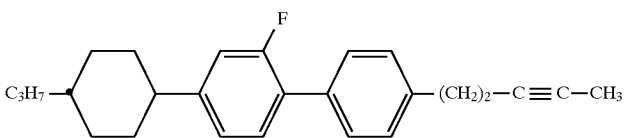|C 88.9 N 143.5 I|
|56|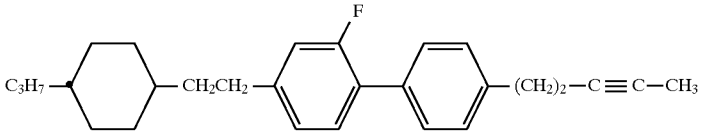| |
|57| | |

| No. | |
|---|---|
| 58 | C₃H₇—⟨cyclohexyl⟩—CH₂CH₂—⟨2,6-F₂-phenyl⟩—⟨phenyl⟩—(CH₂)₂—C≡C—CH₃ |
| 59 | C₃H₇—⟨cyclohexyl⟩—⟨3-F-phenyl⟩—CO₂—⟨phenyl⟩—(CH₂)₂—C≡C—CH₃ |
| 60 | CH₃—CH=CH—CH₂—⟨cyclohexyl⟩—⟨3-F-phenyl⟩—CO₂—⟨phenyl⟩—(CH₂)₂—C≡C—CH₃ |
| 61 | C₃H₇—⟨cyclohexyl⟩—⟨3-F-phenyl⟩—CF₂O—⟨phenyl⟩—(CH₂)₂—C≡C—CH₃ |
| 62 | C₃H₇—⟨cyclohexyl⟩—⟨3-F-phenyl⟩—CF=CF—⟨phenyl⟩—(CH₂)₂—C≡C—CH₃ |
| 63 | C₃H₇—⟨cyclohexyl⟩—(CH₂)₄—⟨phenyl⟩—⟨3-F-phenyl⟩—(CH₂)₂—C≡C—CH₃ |
| 64 | C₃H₇—⟨cyclohexyl⟩—(CH₂)₃O—⟨phenyl⟩—⟨3-F-phenyl⟩—(CH₂)₂—C≡C—CH₃ |
| 65 | C₃H₇—⟨phenyl⟩—⟨phenyl⟩—⟨phenyl⟩—(CH₂)₂—C≡C—CH₃ |
| 66 | CF₃O—⟨3-F-phenyl⟩—⟨phenyl⟩—⟨phenyl⟩—(CH₂)₂—C≡C—CH₃ |
| 67 | CF₃O—⟨phenyl⟩—⟨3-F-phenyl⟩—⟨phenyl⟩—(CH₂)₂—C≡C—CH₃ |
| 68 | CF₃CF₂O—⟨phenyl⟩—⟨3-F-phenyl⟩—⟨phenyl⟩—(CH₂)₂—C≡C—CH₃ |

-continued

| No. | |
|---|---|
| 69 | CF₂CH₂O—[C₆H₄]—[C₆H₃(F)]—[C₆H₄]—(CH₂)₂—C≡C—CH₃ |
| 70 | HCF₂O—[C₆H₄]—[C₆H₃(F)]—[C₆H₄]—(CH₂)₂—C≡C—CH₃ |
| 71 | C₃H₇O—[C₆H₂(F)(F)]—[C₆H₄]—[C₆H₄]—(CH₂)₂—C≡C—CH₃ |
| 72 | C₃H₇—[C₆H₄]—[C₆H₂(F)(F)]—[C₆H₄]—(CH₂)₂—C≡C—CH₃ |
| 73 | C₃H₇O—[C₆H₄]—[C₆H₂(F)(F)]—[C₆H₂(F)(F)]—(CH₂)₂—C≡C—CH₃ |
| 74 | C₃H₇—[C₆H₄]—[C₆H₃(F)]—[C₆H₄]—(CH₂)₂—C≡C—CH₃ |
| 75 | F(CH₂)₃—[C₆H₄]—[C₆H₃(F)]—[C₆H₄]—(CH₂)₂—C≡C—CH₃ |
| 76 | C₃H₇—[C₆H₄]—CH₂CH₂—[C₆H₃(F)]—[C₆H₄]—(CH₂)₂—C≡C—CH₃ |
| 77 | C₃H₇—[C₆H₄]—CH₂CH₂—[C₆H₃(F)]—[C₆H₄]—CH₂C≡C—C₂H₅ |
| 78 | C₃H₇—[C₆H₄]—CH₂CH₂—[C₆H₃(F)]—[C₆H₄]—(CH₂)₇—C≡C—CH₃ |
| 79 | C₃H₇O—[C₆H₃(F)]—[C₆H₄]—CH₂CH₂—[C₆H₄]—(CH₂)₂—C≡C—CH₃ |

-continued

| No. | | |
|---|---|---|
| 80 | C5H11—⌬—⌬—CF=CF—⌬—(CH2)2—C≡C—CH3 | |
| 81 | C5H11—⌬—⌬—CF2O—⌬—(CH2)2—C≡C—CH3 | |
| 82 | C3H7—⌬—C≡C—⌬—C≡C—⌬—(CH2)2—C≡C—CH3 | |
| 83 | C3H7—⌬—C≡C—⌬(F)—C≡C—⌬—(CH2)2—C≡C—CH3 | |
| 84 | C5H11—⌬—C≡C—⌬(F)—C≡C—⌬—(CH2)2—C≡C—CH3 | |
| 85 | C3H7—⌬—C≡C—⌬(F)—C≡C—⌬—(CH2)2—C≡C—CH3 | C 118.0 N 212.8 I, Δε11.0, Δn 0.447 |
| 86 | C5H11—⌬—C≡C—⌬(F)—C≡C—⌬—(CH2)2—C≡C—CH3 | |
| 87 | C3H7—Cy—CH(CH2O)(OCH2)—⌬—(CH2)2—C≡C—CH3 | |
| 88 | CH3CH=CHCH2—Cy—CH(CH2O)(OCH2)—⌬—(CH2)2—C≡C—CH3 | |
| 89 | C3H7—Cy—CH2CH2—CH(CH2O)(OCH2)—⌬—(CH2)2—C≡C—CH3 | |
| 90 | C3H7—CH(CH2O)(OCH2)—⌬—⌬—(CH2)2—C≡C—CH3 | |
| 91 | C3H7—CH(CH2O)(OCH2)—⌬(F,F)—⌬—(CH2)2—C≡C—CH3 | |

-continued
| No. | |
|---|---|
| 92 | 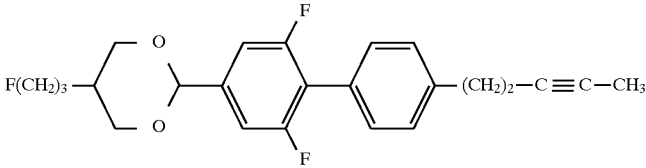 |
| 93 | 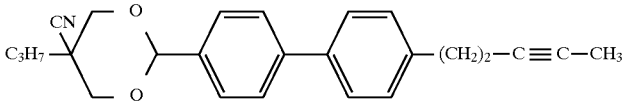 |
| 94 | 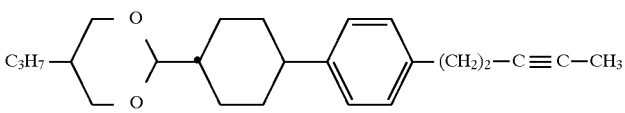 |
| 95 | 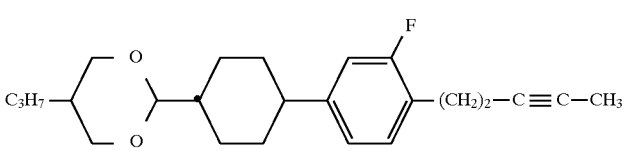 |
| 96 | 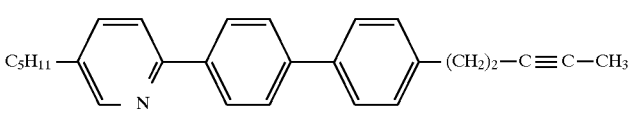 |
| 97 | 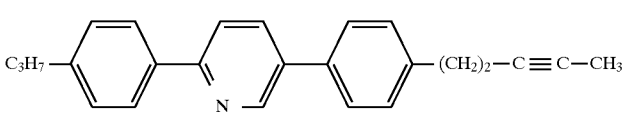 |
| 98 | 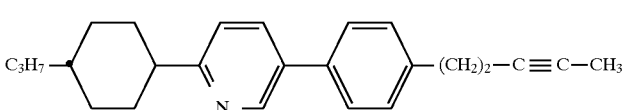 |
| 99 | 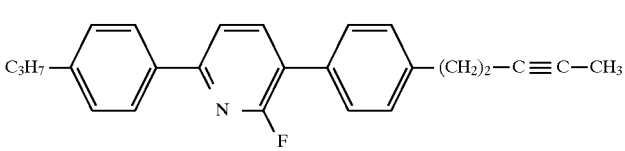 |
| 100 | 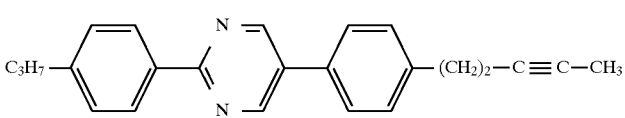 |
| 101 | 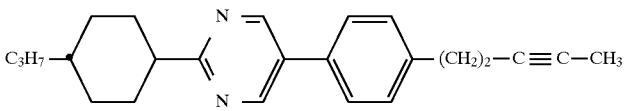 |
| 102 | 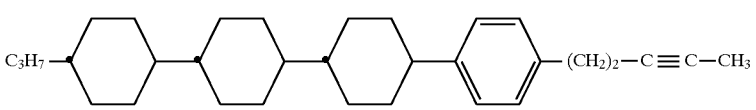 |
| 103 | 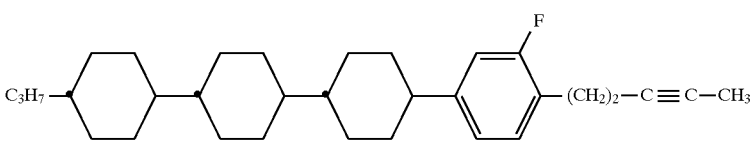 |

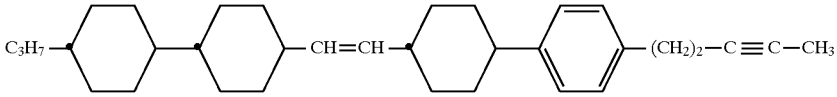

| No. | |
|---|---|
| 117 | 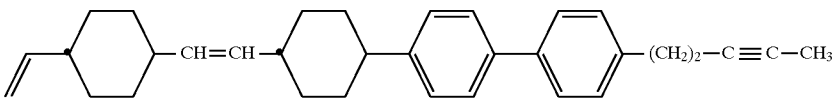 |
| 118 | 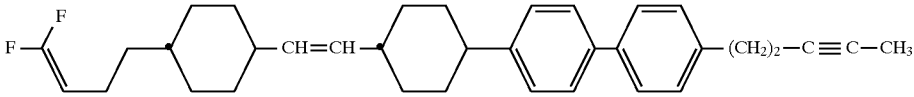 |
| 119 |  |
| 120 |  |
| 121 | 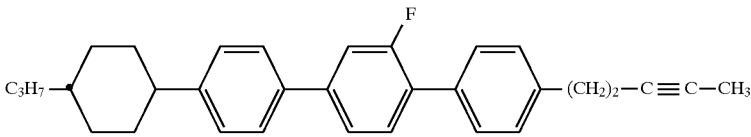 |
| 122 | 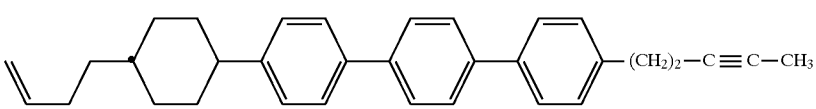 |
| 123 | 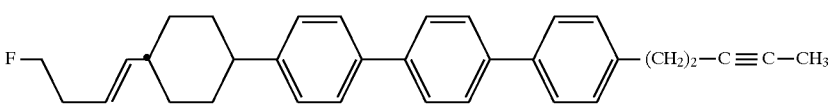 |
| 124 | 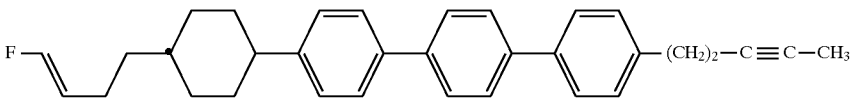 |
| 125 | 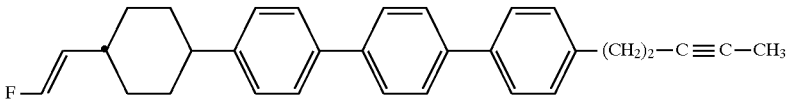 |
| 126 | 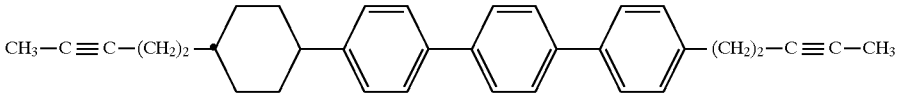 |
| 127 | 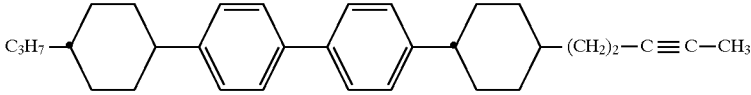 |
| 128 | 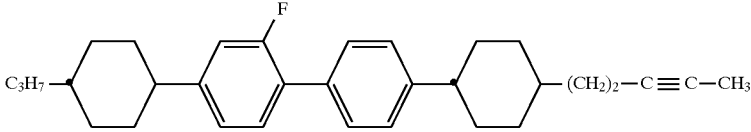 |

Examples of liquid crystal compositions using the liquid crystalline compounds of the present invention as component are shown in Examples 4 through 29 (Use Examples 1 through 26) below.

In each of the Examples, compounds are designated according to the definition shown in the following Table 1. In Table 1, particular groups or structures written in each of columns of left hand side terminal group, bonding group, ring structure, and right hand side terminal group correspond to the symbols written in the same line in the same column. Further, 1,4-cyclohexylene ring in which one or more hydrogen atoms on the ring are substituted with isotope deuterium is designated by H[1D,~8D] instead of H, assuming that 1,4-cyclohexylene is expressed by the formula (21)

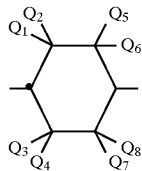

(21)

wherein $Q_1$ to $Q_8$ represent hydrogen atom, and that a particular deuterium substituted for hydrogen atom of $Q_1$ to $Q_8$ is represented by 1D, 2D, 3D, 4D, 5D, 6D, 7D, and 8D, respectively.

Compound number added to the liquid crystalline compounds of the present invention is the same as that shown in Examples. In the Examples, the content of compounds means % by weight or % by part unless otherwise specified.

Data on properties in Use Examples are shown by $T_{NI}$ (clearing point), η (viscosity determined at 20° C.), and Δn, Δε, $V_{th}$ (threshold voltage), and P (pitch length of twist) each of which were determined at 25° C.

TABLE 1

$R+A_1+Z_1-\ldots-Z_n+A_n\rightarrow X$

| | Symbol |
|---|---|
| 1) Left side terminal group R— | |
| $C_nH_{2n+1}-$ | n- |
| $C_nH_{2n+1}O-$ | nO— |
| $C_nH_{2n+1}OC_mH_{2m}-$ | nOm- |
| $CH_2=CH-$ | V— |
| $CH_2=CHC_nH_{2n}-$ | Vn- |
| $C_nH_{2n+1}CH=CHC_mH_{2m}-$ | nVm- |
| $CH_2=CHC_nH_{2n}CH=CH-$ | VnV— |
| $C_nH_{2n+1}CH=CHC_mH_{2m}CH=CHC_kH_{2k}-$ | nVmVk- |
| 2) Ring structure $+A_1+$, $+A_n+$ | |
| 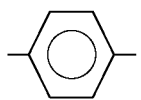 | B |
| 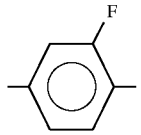 | B(F) |
| 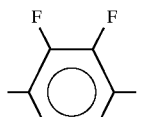 | B(2F,3F) |
| 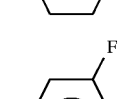 | B(F,F) |
| 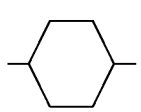 | H |

TABLE 1-continued $R+A_1+Z_1-\ldots-Z_n+A_n\rightarrow X$

| | Symbol |
|---|---|
| pyridine ring | Py |
| dioxane ring | D |
| cyclohexene ring | Ch |
| 3) Bonding group $-Z_1-$, $-Z_n-$ | |
| $-C_2H_4-$ | 2 |
| $-C_4H_8-$ | 4 |
| $-COO-$ | E |
| $-C\equiv C-$ | T |
| $-CH=CH-$ | V |
| $-CF_2O-$ | CF2O |
| $-OCF_2-$ | OCF2 |
| $-CF=CF-$ | CF=CF |
| 4) Right side terminal group $-X$ | |
| $-F$ | $-F$ |
| $-Cl$ | $-CL$ |
| $-CN$ | $-C$ |
| $-CF_3$ | $-CF3$ |
| $-OCF_3$ | $-OCF3$ |
| $-OCF_2H$ | $-OCF2H$ |
| $-C_nH_{2n+1}$ | -n |
| $-OC_nH_{2n+1}$ | $-On$ |
| $-COOCH_3$ | $-EMe$ |
| $-C_nH_{2n}CH=CH_2$ | -nV |
| $-C_mH_{2m}CH=CHC_nH_{2n+1}$ | -mVn |
| $-C_mH_{2m}CH=CHC_nH_{2n}F$ | -mVnF |
| $-CH=CF_2$ | $-VFF$ |
| $-C_nH_{2n}CH=CF_2$ | -nVFF |
| $-C\equiv C-CN$ | $-TC$ |
| $-C_nH_{2n}C\equiv C-H$ | -mT |
| $-C_mH_{2m}-C\equiv C-C_nH_{2n+1}$ | -mTn |
| 5) Examples of designation | |

Example 1    3-H2B(F,F)B(F)-F $C_3H_7-$⬡$-C_2H_4-$⬢$-$⬢$-F$ (with F substituents)

Example 2    3-HB(F)TB-2

$C_3H_7-$⬡$-$⬢$-C\equiv C-$⬢$-C_2H_5$ (with F substituent)

TABLE 1-continued

R$\left(A_1\right)Z_1- \ldots -Z_n\left(A_n\right)$X

| | Symbol |
|---|---|
| Example 3 | 1V2-BEB(F,F)-C |

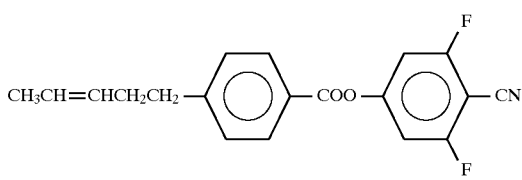

EXAMPLE 4 (Use Example 1)

Liquid crystal composition comprising the following compounds in an amount mentioned below was prepared:

| 3-HH-2T1 | (No. 4) | 7.0% |
|---|---|---|
| 1V2-BEB (F,F)-C | | 5.0% |
| 3-HB-C | | 25.0% |
| 1-BTB-3 | | 5.0% |
| 2-BTB-1 | | 10.0% |
| 3-HH-4 | | 4.0% |
| 3-HHB-1 | | 11.0% |
| 3-HHB-3 | | 9.0% |
| 3-H2BTB-2 | | 4.0% |
| 3-H2BTB-3 | | 4.0% |
| 3-H2BTB-4 | | 4.0% |
| 3-HB(F)TB-2 | | 6.0% |
| 3-HB(F)TB-3 | | 6.0% |

Properties of this composition (primary composition) were determined to find to be as follows:

$T_{NI}$=90.2 (°C.)

η=17.0 (mPa·s)

Δn=0.165

Δε=7.4

$V_{th}$=2.01 (V)

Next, 0.8 part of the compound expressed by the formula (Op-4) was added to 100 parts of the primary composition described above to obtain the secondary composition, and pitch length of liquid crystals in the secondary composition were determined to find to be as follows:

P=12 μm

EXAMPLE 5 (Use Example 2)

Liquid crystal composition comprising the following compounds in an amount mentioned below was prepared:

| 3-HH-2T | (No. 5) | 6.0% |
|---|---|---|
| V2-HB-C | | 12.0% |
| 1V2-HB-C | | 12.0% |
| 3-HB-C | | 15.0% |
| 3-H[1D,2D,3D]B-C | | 9.0% |
| 3-HB[F]-C | | 5.0% |
| 2-BTB-1 | | 2.0% |
| 3-HH-4 | | 2.0% |
| 3-HH-VFF | | 6.0% |
| 2-H[1D,2D,3D]HB-C | | 3.0% |
| 3-HHB-C | | 6.0% |
| 3-HB(F)TB-2 | | 8.0% |
| 3-H2BTB-2 | | 5.0% |
| 3-H2BTB-3 | | 5.0% |
| 3-H2BTB-4 | | 4.0% |

Properties of this composition were determined to find to be as follows:

$T_{NI}$=86.7 (°C.)

η=19.6 (mPa·s)

Δn=0.157

Δε=9.0

$V_{th}$=1.89 (V)

EXAMPLE 6 (Use Example 3)

Liquid crystal composition comprising the following compounds in an amount mentioned below was prepared:

| 3-HH-2T | (No. 5) | 5.0% |
|---|---|---|
| 3-HBB-2T1 | (No. 49) | 6.0% |
| 301-BEB(F)-C | | 15.0% |
| 401-BEB(F)-C | | 13.0% |
| 501-BEB(F)-C | | 13.0% |
| 2-HHB(F)-C | | 15.0% |
| 3-HHB(F)-C | | 15.0% |
| 3-HB(F)TB-2 | | 4.0% |
| 3-HB(F)TB-3 | | 4.0% |
| 3-HB(F)TB-4 | | 4.0% |
| 3-HHB-1 | | 2.0% |
| 3-HHB-O1 | | 4.0% |

EXAMPLE 7 (Use Example 4)

Liquid crystal composition comprising the following compounds in an amount mentioned below was prepared:

| 3-HH-2T1 | (No. 4) | 3.0% |
|---|---|---|
| V-HH-2T1 | (No. 6) | 3.0% |
| V-HVHBB-2T1 | (No. 117) | 4.0% |
| 5-PyB-F | | 4.0% |
| 3-PyB(F)-F | | 4.0% |
| 2-BB-C | | 5.0% |
| 4-BB-C | | 4.0% |
| 5-BB-C | | 5.0% |
| 2-PyB-2 | | 2.0% |
| 3-PyB-2 | | 2.0% |
| 4-PyB-2 | | 2.0% |
| 6-PyB-05 | | 3.0% |
| 6-PyB-06 | | 3.0% |
| 6-PyB-07 | | 3.0% |
| 6-PyB-08 | | 3.0% |
| 3-PyBB-F | | 6.0% |
| 4-PyBB-F | | 6.0% |
| 5-PyBB-F | | 6.0% |
| 3-HHB-3 | | 4.0% |
| 2-H2BTB-2 | | 4.0% |
| 2-H2BTB-3 | | 4.0% |
| 2-H2BTB-4 | | 5.0% |
| 3-H2BTB-2 | | 5.0% |
| 3-H2BTB-3 | | 5.0% |
| 3-H2BTB-4 | | 5.0% |

Properties of this composition were determined to find to be as follows:

$T_{NI}$=91.9 (°C.)

η=38.5 (mPa·s)

Δn=0.203

Δε=6.5

$V_{th}$=2.26 (V)

EXAMPLE 8 (Use Example 5)

Liquid crystal composition comprising the following compounds in an amount mentioned below was prepared:

| | | |
|---|---|---|
| V2V-HHB-2T1 | (No. 33) | 3.0% |
| 3-DB-C | | 10.0% |
| 4-DB-C | | 10.0% |
| 2-BEB-C | | 12.0% |
| 3-BEB-C | | 4.0% |
| 3-PYB(F)-F | | 6.0% |
| 3-HEB-04 | | 8.0% |
| 4-HEB-02 | | 6.0% |
| 5-HEB-01 | | 6.0% |
| 3-HEB-02 | | 5.0% |
| 5-HEB-02 | | 4.0% |
| 5-HEB-5 | | 5.0% |
| 4-HEB-5 | | 5.0% |
| 10-BEB-2 | | 4.0% |
| 3-HHB-1 | | 3.0% |
| 3-HHEBB-C | | 3.0% |
| 3-HBEBB-C | | 3.0% |
| 5-HBEBB-C | | 3.0% |

Properties of this composition were determined to find to be as follows:

$T_{NI}$=69.2 (°C.)

η=40.7 (mPa·s)

Δn=0.123

Δε=11.5

$V_{th}$=1.30 (V)

EXAMPLE 9 (Use Example 6)

Liquid crystal composition comprising the following compounds in an amount mentioned below was prepared:

| | | |
|---|---|---|
| 3-HH-2T | (No. 5) | 8.0% |
| 3-HBB-2T1 | (No. 49) | 8.0% |
| 3-BTB(F)TB-2T1 | (No. 83) | 3.0% |
| 3-HB-C | | 10.0% |
| 7-HB-C | | 3.0% |
| 101-HB-C | | 10.0% |
| 3-HB(F)-C | | 10.0% |
| 2-PyB-2 | | 2.0% |
| 3-PyB-2 | | 2.0% |
| 4-PyB-2 | | 2.0% |
| 101-HH-3 | | 7.0% |
| 2-BTB-01 | | 7.0% |
| 3-HHB-1 | | 7.0% |
| 3-HHB-F | | 4.0% |
| 3-HHB-01 | | 4.0% |
| 3-H2BTB-2 | | 3.0% |
| 2-PyBH-3 | | 4.0% |
| 3-PyBH-3 | | 3.0% |
| 3-PyBH-2 | | 3.0% |

EXAMPLE 10 (Use Example 7)

Liquid crystal composition comprising the following compounds in an amount mentioned below was prepared:

| | | |
|---|---|---|
| 3-HH-2T1 | (No. 4) | 5.0% |
| V2V-HHB-2T1 | (No. 33) | 50% |
| 201-BEB(F)-C | | 5.0% |
| 301-BEB(F)-C | | 12.0% |
| 501-BEB (F)-C | | 4.0% |
| 1V2-BEB(F,F)-C | | 10.0% |
| 3-HH-EMe | | 10.0% |
| 3-HB-02 | | 18.0% |
| 7-HEB-F | | 2.0% |
| 3-HHEB-F | | 2.0% |
| 5-HHEB-F | | 2.0% |
| 3-HBEB-F | | 4.0% |
| 201-HBEB(F)-C | | 2.0% |

-continued

| | | |
|---|---|---|
| 3-HB(F)EB(F)-C | | 2.0% |
| 3-HBEB(F,F)-C | | 2.0% |
| 3-HHB-F | | 4.0% |
| 3-HHB-01 | | 4.0% |
| 3-HHB-3 | | 3.0% |
| 3-HEBEB-F | | 2.0% |
| 3-HEBEB-1 | | 2.0% |

Properties of this composition were determined to find to be as follows:

$T_{NI}$=73.7 (°C.)

η=38.3 (mPa·s)

Δn=0.117

Δε=23.6

$V_{th}$=0.94 (V)

While this composition was left at −20° C., separation of crystals or a smectic phase was not confirmed at the time when 30 days passed.

EXAMPLE 11 (Use Example 8)

Liquid crystal composition comprising the following compounds in an amount mentioned below was prepared:

| | | |
|---|---|---|
| 3-HH-2T | (No. 5) | 5.0% |
| V-HVHBB-2T1 | (No. 117) | 5.0% |
| 5-BEB(F)-C | | 5.0% |
| V-HB-C | | 11.0% |
| 5-PyB-C | | 6.0% |
| 4-EB-3 | | 11.0% |
| 3-HH-2V | | 10.0% |
| 5-HH-V | | 11.0% |
| V-HHB-1 | | 7.0% |
| V2-HHB-1 | | 15.0% |
| 3-HHB-1 | | 4.0% |
| 1V2-HBB-2 | | 5.0% |
| 3-HHEBH-3 | | 5.0% |

Properties of this composition were determined to find to be as follows:

$T_{NI}$=82.8 (°C.)

η=16.3 (mPa·s)

Δn=0.112

Δε=4.8

$V_{th}$=2.36 (V)

EXAMPLE 12 (Use Example 9)

Liquid crystal composition comprising the following compounds in an amount mentioned below was prepared:

| | | |
|---|---|---|
| V-HH-2T1 | (No. 6) | 7.0% |
| V-HVHBB-2T1 | (No. 117) | 7.0% |
| V2V-HHB-2T1 | (No. 33) | 5.0% |
| 3-BTB(F)TB-2T1 | (No. 83) | 8.0% |
| 201-BEB(F)-C | | 5.0% |
| 301-BEB(F)-C | | 12.0% |
| 501-BEB(F)-C | | 4.0% |
| 1V2-BEB (F,F)-C | | 16.0% |
| 3-HB-02 | | 3.0% |
| 3-HH-4 | | 3.0% |
| 3-HHB-F | | 3.0% |
| 3-HHB-1 | | 3.0% |
| 3-HHB-01 | | 4.0% |
| 3-HBEB-F | | 4.0% |
| 3-HHEB-F | | 7.0% |

| | | |
|---|---|---|
| 3-H2BTB-2 | | 4.0% |
| 3-HB(F)TB-2 | | 5.0% |

Properties of this composition were determined to find to be as follows:

$T_{NI}$=89.4 (°C.)

$\eta$=49.8 (mPa·s)

$\Delta n$=0.172

$\Delta \epsilon$=28.3

$V_{th}$=1.00 (V)

EXAMPLE 13 (Use Example 10)

Liquid crystal composition comprising the following compounds in an amount mentioned below was prepared:

| | | |
|---|---|---|
| V-HH-2T1 | (No. 6) | 2.0% |
| 2-BEB-C | | 12.0% |
| 3-BEB-C | | 4.0% |
| 4-BEB-C | | 6.0% |
| 3-HB-C | | 28.0% |
| 3-HEB-04 | | 12.0% |
| 4-HEB-02 | | 8.0% |
| 5-HEB-01 | | 8.0% |
| 3-HEB-02 | | 6.0% |
| 5-HEB-02 | | 5.0% |
| 3-HHB-1 | | 5.0% |
| 3-HHB-01 | | 4.0% |

Properties of this composition were determined to find to be as follows:

$T_{NI}$=60.3 (°C.)

$\eta$=25.7 (mPa·s)

$\Delta n$=0.112

$\Delta \epsilon$=10.0

$V_{th}$=1.35 (V)

EXAMPLE 14 (Use Example 11)

Liquid crystal composition comprising the following compounds in an amount mentioned below was prepared:

| | | |
|---|---|---|
| 3-BTB(F)TB-2T1 | (No. 83) | 10.0% |
| V-HVHBB-2T1 | (No. 117) | 3.0% |
| 2-BEB-C | | 10.0% |
| 5-BB-C | | 12.0% |
| 7-BB-C | | 7.0% |
| 1-BTB-3 | | 7.0% |
| 10-BEB-2 | | 10.0% |
| 10-BEB-5 | | 12.0% |
| 2-HHB-1 | | 4.0% |
| 3-HHB-F | | 4.0% |
| 3-HHB-1 | | 7.0% |
| 3-HHB-01 | | 4.0% |
| 3-HHB-3 | | 10.0% |

Properties of this composition were determined to find to be as follows:

$T_{NI}$=86.4 (°C.)

$\eta$=29.0 (mPa·s)

$\Delta n$=0.188

$\Delta \epsilon$=6.9

$V_{th}$=1.49 (V)

EXAMPLE 15 (Use Example 12)

Liquid crystal composition comprising the following compounds in an amount mentioned below was prepared:

| | | |
|---|---|---|
| 3-BCF = CFB-2T1 | (No. 21) | 10.0% |
| 3-BTB(F)TB-2T1 | (No. 83) | 4.0% |
| 1V2-BEB(F,F)-C | | 8.0% |
| 3-HB-C | | 10.0% |
| V2V-HB-C | | 14.0% |
| V2V-HH-3 | | 19.0% |
| 3-HB-02 | | 4.0% |
| 3-HHB-1 | | 10.0% |
| 3-HHB-3 | | 5.0% |
| 3-HB(F)TB-2 | | 4.0% |
| 3-HB(F)TB-3 | | 4.0% |
| 3-H2BTB-2 | | 4.0% |
| 3-H2BTB-3 | | 4.0% |

Properties of this composition were determined to find to be as follows:

$T_{NI}$=94.2 (°C.)

$\eta$=19.6 (mPa·s)

$\Delta n$=0.156

$\Delta \epsilon$=8.4

$V_{th}$=1.72 (V)

EXAMPLE 16 (Use Example 13)

Liquid crystal composition comprising the following compounds in an amount mentioned below was prepared:

| | | |
|---|---|---|
| 3-HH-2T | (No. 5) | 5.0% |
| 3-BTB(F)TB-2T1 | (No. 83) | 3.0% |
| 5-BTB(F)TB-3 | | 10.0% |
| V2-HB-TC | | 10.0% |
| 3-HB-TC | | 10.0% |
| 3-HB-C | | 10.0% |
| 5-HB-C | | 7.0% |
| 5-BB-C | | 3.0% |
| 2-BTB-1 | | 10.0% |
| 2-BTB-01 | | 5.0% |
| 3-HH-4 | | 5.0% |
| 3-HHB-1 | | 5.0% |
| 3-HHB-3 | | 11.0% |
| 3-H2BTB-2 | | 3.0% |
| 3-HB(F)TB-2 | | 3.0% |

Properties of this composition were determined to find to be as follows:

$T_{NI}$=96.5 (°C.)

$\eta$=15.7 (mPa·s)

$\Delta n$=0.209

$\Delta \epsilon$=6.8

$V_{th}$=2.10 (V)

EXAMPLE 17 (Use Example 14)

Liquid crystal composition comprising the following compounds in an amount mentioned below was prepared:

| | | |
|---|---|---|
| V2V—HHB-2T1 | (No. 33) | 4.0% |
| 3-BCF=CFB-2T1 | (No. 21) | 2.0% |
| 1V2-BEB(F,F)—C | | 6.0% |
| 3-HB—C | | 18.0% |
| 2-BTB-1 | | 10.0% |
| 5-HH—VFF | | 30.0% |
| 1-BHH—VFF | | 8.0% |
| 1-BHH-2VFF | | 11.0% |
| 3-H2BTB-2 | | 5.0% |
| 3-H2BTB-3 | | 4.0% |
| 3-HHB-1 | | 2.0% |

Properties of this composition were determined to find to be as follows:

$T_{NI}$=79.8 (°C.)

η=13.9 (mPa·s)

Δn=0.132

Δε=6.5

$V_{th}$=2.07 (V)

EXAMPLE 18 (Use Example 15)

Liquid crystal composition comprising the following compounds in an amount mentioned below was prepared:

| | |
|---|---|
| 3-HH-2T1 (No. 4) | 5.0% |
| V2V—HHB-2T1 (No. 33) | 5.0% |
| 2-HB—C | 5.0% |
| 3-HB—C | 12.0% |
| 3-HB—O2 | 15.0% |
| 2-BTB-1 | 3.0% |
| 3-HHB-1 | 8.0% |
| 3-HHB—F | 4.0% |
| 3-HHB—O1 | 5.0% |
| 3-HHB-3 | 4.0% |
| 3-HHEB—F | 4.0% |
| 5-HHEB—F | 4.0% |
| 2-HHB(F)—F | 7.0% |
| 3-HHB(F)—F | 7.0% |
| 5-HHB(F)—F | 7.0% |
| 3-HHB(F,F)—F | 5.0% |

Properties of this composition were determined to find to be as follows:

$T_{NI}$=97.9 (°C.)

η=21.2 (mPa·s)

Δn=0.102

Δε=4.7

$V_{th}$=2.42 (V)

EXAMPLE 19 (Use Example 16)

Liquid crystal composition comprising the following compounds in an amount mentioned below was prepared:

| | |
|---|---|
| 3-HH-2T1 (No. 4) | 6.0% |
| 2-HHB(F)—F | 17.0% |
| 3-HHB(F)—F | 17.0% |
| 5-HHB(F)—F | 16.0% |
| 2-H2HB(F)—F | 10.0% |
| 3-H2HB(F)—F | 5.0% |
| 5-H2HB(F)—F | 10.0% |
| 3-HBB(F)—F | 6.0% |
| 5-HBB(F)—F | 13.0% |

Properties of this composition (primary composition) were determined to find to be as follows:

$T_{NI}$=99.2 (°C.)

η=24.1 (mPa·s)

Δn=0.092

Δε=4.9

$V_{th}$=2.41 (V)

Next, 0.3 part of the compound expressed by the formula (Op-8) was added to 100 parts of the primary composition described above to obtain the secondary composition, and pitch length of liquid crystals in the secondary composition were determined to find to be as follows:

P=81 μm

EXAMPLE 20 (Use Example 17)

Liquid crystal composition comprising the following compounds in an amount mentioned below was prepared:

| | |
|---|---|
| 3-HH-2T (No. 5) | 3.0% |
| 7-HB(F)—F | 5.0% |
| 5-H2B(F)—F | 5.0% |
| 3-HB—O2 | 10.0% |
| 3-HH-4 | 2.0% |
| 3-HH[5D,6D,7D]-4 | 3.0% |
| 2-HHB(F)—F | 10.0% |
| 3-HHB(F)—F | 10.0% |
| 5-HH[5D,6D,7D]B(F)—F | 10.0% |
| 3-H2HB(F)—F | 5.0% |
| 3-HBB(F)—F | 3.0% |
| 5-HBB(F)—F | 6.0% |
| 2-H2BB(F)—F | 5.0% |
| 3-H2BB(F)—F | 6.0% |
| 3-HHB-1 | 8.0% |
| 3-HHB—O1 | 5.0% |
| 3-HHB-3 | 4.0% |

Properties of this composition (primary composition) were determined to find to be as follows:

$T_{NI}$=88.2 (°C.)

η=17.4 (mPa·s)

Δn=0.093

Δε=3.2

$V_{th}$=2.77 (V)

EXAMPLE 21 (Use Example 18)

Liquid crystal composition comprising the following compounds in an amount mentioned below was prepared:

| | |
|---|---|
| 3-HH-2T1 (No. 4) | 9.0% |
| 7-HB(F,F)—F | 3.0% |
| 3-HB—O2 | 7.0% |
| 2-HHB(F)—F | 10.0% |
| 3-HHB(F)—F | 10.0% |
| 5-HHB(F)—F | 10.0% |
| 3-HBB(F)—F | 9.0% |
| 5-HBB(F)—F | 16.0% |
| 2-HBB—F | 4.0% |
| 3-HBB—F | 4.0% |
| 5-HBB—F | 3.0% |
| 3-HBB(F,F)—F | 5.0% |
| 5-HBB(F,F)—F | 10.0% |

EXAMPLE 22 (Use Example 19)

Liquid crystal composition comprising the following compounds in an amount mentioned below was prepared:

| | |
|---|---|
| V—HH-2T1 (No. 6) | 5.0% |
| 7-HB(F,F)—F | 3.0% |
| 3-H2HB(F,F)—F | 12.0% |
| 4-H2HB(F,F)—F | 10.0% |
| 5-H2HB(F,F)—F | 10.0% |
| 3-HHB(F,F)—F | 5.0% |
| 3-HH2B(F,F)—F | 15.0% |
| 5-HH2B(F,F)—F | 10.0% |
| 3-HBB(F,F)—F | 12.0% |
| 5-HBB(F,F)—F | 12.0% |
| 3-HBCF2OB(F,F)—F | 6.0% |

Properties of this composition (primary composition) were determined to find to be as follows:

$T_{NI}$=71.6 (°C.)

η=24.7 (mPa·s)

Δn=0.087

Δε=8.4

$V_{th}$=1.78 (V)

EXAMPLE 23 (Use Example 20)

Liquid crystal composition comprising the following compounds in an amount mentioned below was prepared:

| | |
|---|---|
| V2V—HHB-2T1 (No. 33) | 5.0% |
| 7-HB(F,F)—F | 5.0% |
| 3-H2HB(F,F)—F | 12.0% |
| 4-H2HB(F,F)—F | 10.0% |
| 3-HHB(F,F)—F | 10.0% |
| 3-HBB(F,F)—F | 10.0% |
| 3-HHEB(F,F)—F | 10.0% |
| 4-HHEB(F,F)—F | 3.0% |
| 5-HHEB(F,F)—F | 3.0% |
| 2-HBEB(F,F)—F | 3.0% |
| 3-HBEB(F,F)—F | 5.0% |
| 5-HBEB(F,F)—F | 3.0% |
| 3-HDB(F,F)—F | 15.0% |
| 3-HHBB(F,F)—F | 6.0% |

Properties of this composition (primary composition) were determined to find to be as follows:

$T_{NI}$=79.8 (°C.)

$\eta$=35.6 (mPa·s)

$\Delta n$=0.092

$\Delta\epsilon$=12.8

$V_{th}$=1.51 (V)

EXAMPLE 24 (Use Example 21)

Liquid crystal composition comprising the following compounds in an amount mentioned below was prepared:

| | |
|---|---|
| 3-BTB(F)TB-2T1 (No. 83) | 4.0% |
| 3-HB—CL | 10.0% |
| 5-HB—CL | 4.0% |
| 7-HB—CL | 4.0% |
| 1O1-HH-5 | 5.0% |
| 2-HBB(F)—F | 8.0% |
| 3-HBB(F)—F | 8.0% |
| 5-HBB(F)—F | 14.0% |
| 4-HHB—CL | 8.0% |
| 5-HHB—CL | 8.0% |
| 3-H2HB(F)—CL | 4.0% |
| 3-HBB(F,F)—F | 10.0% |
| 5-H2BB(F,F)—F | 9.0% |
| 3-HB(F)VB-2 | 4.0% |

Properties of this composition (primary composition) were determined to find to be as follows:

$T_{NI}$=91.9 (°C.)

$\eta$=22.1 (mPa·s)

$\Delta n$=0.138

$\Delta\epsilon$=5.2

$V_{th}$=2.16 (V)

EXAMPLE 25 (Use Example 22)

Liquid crystal composition comprising the following compounds in an amount mentioned below was prepared:

| | |
|---|---|
| 3-BCF=CFB-2T1 (No. 21) | 2.0% |
| V—HVHBB-2T1 (No. 117) | 2.0% |
| 3-HHB(F,F)—F | 9.0% |
| 3-H2HB(F,F)—F | 8.0% |
| 4-H2HB(F,F)—F | 8.0% |
| 5-H2HB(F,F)—F | 8.0% |
| 3-HBB(F,F)—F | 21.0% |
| 5-HBB(F,F)—F | 20.0% |
| 3-H2BB(F,F)—F | 10.0% |
| 5-HHBB(F,F)—F | 3.0% |
| 5-HHEBB—F | 2.0% |
| 3-HH2BB(F,F)—F | 3.0% |
| 1O1-HBBH-5 | 4.0% |

Properties of this composition (primary composition) were determined to find to be as follows:

$T_{NI}$=94.2 (°C.)

$\eta$=34.5 (mPa·s)

$\Delta n$=0.119

$\Delta\epsilon$=9.1

$V_{th}$=1.69 (V)

EXAMPLE 26 (Use Example 23)

Liquid crystal composition comprising the following compounds in an amount mentioned below was prepared:

| | |
|---|---|
| 3-HBB-2T1 (No. 49) | 5.0% |
| V—HVHBB-2T1 (No. 117) | 5.0% |
| 5-HB—F | 12.0% |
| 6-HB—F | 9.0% |
| 7-HB—F | 7.0% |
| 2-HHB—OCF3 | 7.0% |
| 3-HHB—OCF3 | 7.0% |
| 4-HHB—OCF3 | 7.0% |
| 5-HHB—OCF3 | 5.0% |
| 3-HH2B—OCF3 | 4.0% |
| 5-HH2B—OCF3 | 4.0% |
| 3-HHB(F,F)—OCF3 | 5.0% |
| 5-HBB(F)—F | 10.0% |
| 3-HH2B(F)—F | 3.0% |
| 3-HB(F)BH-3 | 3.0% |
| 5-HBBH-3 | 3.0% |
| 3-HHB(F,F)—OCF2H | 4.0% |

EXAMPLE 27 (Use Example 24)

Liquid crystal composition comprising the following compounds in an amount mentioned below was prepared:

| | |
|---|---|
| V2V—HHB-2T1 (No. 33) | 3.0% |
| 5-H4HB(F,F)—F | 7.0% |
| 5-H4HB—OCF3 | 15.0% |
| 3-H4HB(F,F)—CF3 | 8.0% |
| 5-H4HB(F,F)—CF3 | 10.0% |
| 3-HB—CL | 6.0% |
| 5-HB—CL | 4.0% |
| 2-H2BB(F)—F | 5.0% |
| 3-H2BB(F)—F | 10.0% |
| 5-HVHB(F,F)—F | 5.0% |
| 3-HHB—OCF3 | 5.0% |
| 3-H2HB—OCF3 | 5.0% |
| V—HHB(F)—F | 5.0% |
| 3-HHB(F)—F | 2.0% |
| 5-HHEB—OCF3 | 2.0% |
| 3-HBEB(F,F)—F | 5.0% |
| 5-HH—V2F | 3.0% |

Properties of this composition (primary composition) were determined to find to be as follows:

$T_{NI}$=67.3 (°C.)

$\eta$=26.2 (mPa·s)

$\Delta n$=0.097

$\Delta\epsilon$=8.2

$V_{th}$=1.83 (V)

EXAMPLE 28 (Use Example 25)

Liquid crystal composition comprising the following compounds in an amount mentioned below was prepared:

| | |
|---|---|
| 3-HH-2T (No. 5) | 2.0% |
| V—HH-2T1 (No. 6) | 2.0% |
| 3-BTB(F)TB-2T1 (No. 83) | 2.0% |
| 2-HHB(F)—F | 2.0% |
| 3-HHB(F)—F | 2.0% |
| 5-HHB(F)—F | 2.0% |
| 3-HBB(F)—F | 6.0% |
| 5-HBB(F)—F | 10.0% |
| 2-H2BB(F)—F | 9.0% |
| 3-H2BB(F)—F | 9.0% |
| 3-HBB(F,F)—F | 25.0% |
| 5-HBB(F,F)—F | 19.0% |
| 1O1-HBBH-4 | 5.0% |
| 1O1-HBBH-5 | 5.0% |

Properties of this composition (primary composition) were determined to find to be as follows:

$T_{NI}$=99.1 (°C.)

$\eta$=34.7 (mPa·s)

$\Delta n$=0.142

$\Delta\epsilon$=7.3

$V_{th}$=1.91 (V)

EXAMPLE 29 (Use Example 26)

Liquid crystal composition comprising the following compounds in an amount mentioned below was prepared:

| | |
|---|---|
| 3-HH-2T (No. 5) | 2.0% |
| 3-HBB-2T1 (No. 49) | 2.0% |
| 5-HB—CL | 12.0% |
| 3-HH-4 | 3.0% |
| 3-HB—O2 | 20.0% |
| 3-H2HB(F,F)—F | 8.0% |
| 3-HHB(F,F)—F | 8.0% |
| 3-HBB(F,F)—F | 6.0% |
| 2-HHB(F)—F | 5.0% |
| 3-HHB(F)—F | 5.0% |
| 5-HHB(F)—F | 5.0% |
| 2-H2HB(F)—F | 2.0% |
| 3-H2HB(F)—F | 1.0% |
| 5-H2HB(F)—F | 2.0% |
| 3-HHBB(F,F)—F | 4.0% |
| 3-HBCF2OB—OCF3 | 4.0% |
| 5-HBCF2OB(F,F)—CF3 | 4.0% |
| 3-HHB-1 | 3.0% |
| 3-HHB—O1 | 4.0% |

Comparative Example 1

Liquid crystal composition was prepared in the same manner as in Example 10 (Use Example 7) with the exception that V2V-HHB-2T1 (No. 83) was replaced by 3-HHB-5. When this composition was left at −20° C., formation of crystals was observed 3 days after.

As demonstrated above, the liquid crystal compositions of the present invention have an excellent chemical stability in addition to a remarkably high $\Delta n$ and a good miscibility with other liquid crystalline compounds, and thus, the compounds of the present invention can be said to be remarkably improved compared with conventional liquid crystal compounds.

Accordingly, it can be understood that when the liquid crystalline compounds of the present invention are used as component of liquid crystal compositions, the compounds can be used for liquid crystal compositions particularly for STN which has most generally been used.

We claim:

1. A liquid crystalline compound expressed by the general formula (1)

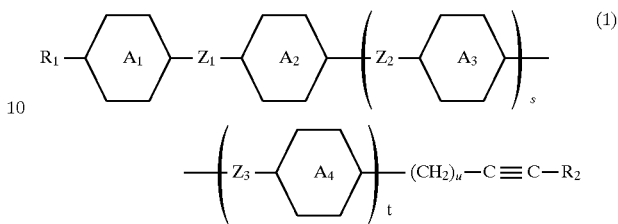

wherein $R_1$ represents a halogen atom, cyano group, or an alkyl group, alkenyl group, alkynyl group, alkoxy group, alkoxyalkyl group, alkenyloxy group, alkynyloxy group, or alkadienyl group having 1 to 15 carbon atoms in which group (excluding cyano group) hydrogen atom may be replaced by fluorine atom, chlorine atom, or cyano group, and one or not-adjacent two or more methylene groups may be replaced by oxygen atom, —CH=CH— or —C≡C—; $R_2$ represents an alkyl group having 1 to 10 carbon atoms; rings $A_1$, $A_2$, $A_3$, and $A_4$ independently represent 1,4-cyclohexylene, 1,4-phenylene, 1,3-dioxane-2,5-diyl, pyridine-2,5-diyl, or pyrimidine-2,5-diyl in all of which hydrogen atom may be replaced by a halogen atom or cyano group; $Z_1$, $Z_2$, and $Z_3$ independently represent a covalent bond, —CH$_2$CH$_2$—, —CH=CH—, —C≡C—, —CH$_2$O—, —OCH$_2$—, —(CH$_2$)$_4$-, —(CH$_2$)$_3$—O—, —O—(CH$_2$)$_3$-, —(CH$_2$)$_2$—CH=CH—, —CH=CH—(CH$_2$)$_2$-, —C≡C—CH=CH—, —CH=CH—C≡C—, —CF$_2$O—, —OCF$_2$—, —CF=CF—, —CO$_2$—, or —OCO—, provided that in no case does only one of $Z_1$, $Z_2$ and $Z_3$ represent —C≡C— between two 1,4-phenylene rings; s and t are independently an integer of 0 or 1; u is an integer of 1 to 5; and each of the elements in the general formula may be its isotope.

2. The liquid crystalline compound according to claim 1 wherein $R_1$ is an alkyl group, alkenyl group, alkynyl group, or alkoxy group; and both s and t are 0.

3. The liquid crystalline compound according to claim 1 wherein $R_1$ is an alkyl group, alkenyl group, alkynyl group, or alkoxy group; s is 1; and t is 0.

4. The liquid crystalline compound according to claim 1 wherein $R_1$ is an alkyl group, alkenyl group, alkynyl group, or alkoxy group; and both s and t are 1.

5. The liquid crystalline compound according to claim 2 wherein both rings $A_1$ and $A_2$ are 1,4-cyclohexylene; and $Z_1$ is a covalent bond or —CH=CH—.

6. The liquid crystalline compound according to claim 2 wherein ring $A_2$ is 1,4-phenylene in which hydrogen atom may be replaced by a halogen atom; ring $A_1$ is 1,4-cyclohexylene, 1,4-phenylene, 1,3-dioxane-2,5-diyl, pyridine-2,5-diyl, or pyrimidine-2,5-diyl in all of which hydrogen atom may be replaced by a halogen atom; and $Z_1$ is a covalent bond or —CF=CF—.

7. The liquid crystalline compound according to claim 3 wherein ring $A_3$ is 1,4-cyclohexylene; and $Z_1$ and $Z_2$ are independently a covalent bond, —CH$_2$CH$_2$—, —CH=CH—, or —CF=CF—.

8. The liquid crystalline compound according to claim 3 wherein ring $A_3$ is 1,4-phenylene in which hydrogen atom may be replaced by a halogen atom; and $Z_1$ and $Z_2$ are independently a covalent bond, —CH$_2$CH$_2$—, —CH=CH—, —C≡C—, or —CF=CF—.

9. The liquid crystalline compound according to claim 4 wherein ring $A_4$ is 1,4-cyclohexylene; and $Z_1$, $Z_2$, and $Z_3$ are independently a covalent bond, —$CH_2CH_2$—, —CH=CH—, —C≡C—, or —CF=CF—.

10. The liquid crystalline compound according to claim 4 wherein ring $A_4$ is 1,4-phenylene in which hydrogen atom may be replaced by a halogen atom; and $Z_1$, $Z_2$, and $Z_3$ are independently a covalent bond, —$CH_2CH_2$—, —CH=CH—, —C≡C—, or —CF=CF—.

11. A liquid crystal composition comprising at least one liquid crystalline compound defined in claim 1, and at least one other compound.

12. A liquid crystal composition comprising, as a first component, at least one liquid crystalline compound defined in claim 1, and, as a second component, at least one compound selected from the group consisting of the compounds expressed by any one of the general formulas (2), (3), and (4)

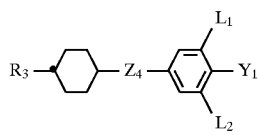  (2)

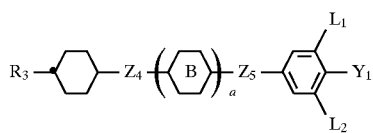  (3)

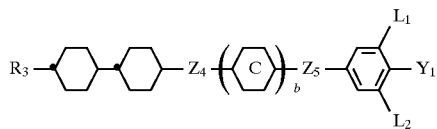  (4)

wherein $R_3$ represents an alkyl group having 1 to 10 carbon atoms in which group one or not-adjacent two or more methylene groups may be replaced by oxygen atom or —CH=CH—, and any hydrogen atom may be replaced by fluorine atom; $Y_1$ represents fluorine atom, chlorine atom, —$OCF_3$, —$OCF_2H$, —$CF_3$, —$CF_2H$, —$CFH_2$, —$OCF_2CF_2H$, or —$OCF_2CFHCF_3$; $L_1$ and $L_2$ independently represent hydrogen atom or fluorine atom; $Z_4$ and $Z_5$ independently represent —$CH_2CH_2$—, —$(CH_2)_4$-, —CO2—, —$CF_2O$—, —$OCF_2$—, —CH=CH—, or a covalent bond; ring B represents 1,4-cyclohexylene, 1,3-dioxane-2,5-diyl, or 1,4-phenylene in which phenylene any hydrogen atom may be replaced by fluorine atom; ring C represents 1,4-cyclohexylene, or 1,4-phenylene in which phenylene any hydrogen atom may be replaced by fluorine atom; a and b are independently 0 or 1; and each of the elements in the general formulas may be its isotope.

13. A liquid crystal composition comprising, as a first component, at least one liquid crystalline compound defined in claim 1, and, as a second component, at least one compound selected from the group consisting of the compounds expressed by the general formula (5) or (6)

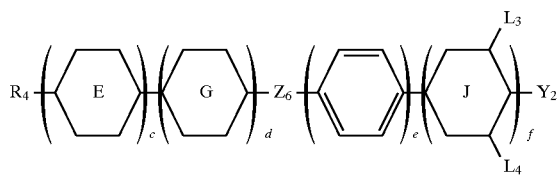  (5)

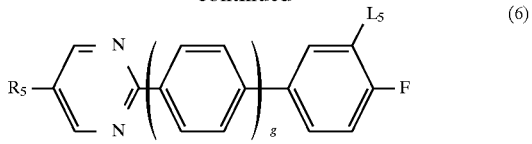  (6)

wherein $R_4$ and $R_5$ independently represent an alkyl group having 1 to 10 carbon atoms in which group one or not-adjacent two or more methylene groups may be replaced by oxygen atom or —CH=CH—, and any hydrogen atom may be replaced by fluorine atom; $Y_2$ represents —CN group or —C≡C—CN; ring E represents 1,4-cyclohexylene, 1,4-phenylene, 1,3-dioxane-2,5-diyl, or pyrimidine-2,5-diyl; ring G represents 1,4-cyclohexylene, 1,4-phenylene in which phenylene hydrogen atom may be replaced by fluorine atom, or pyrimidine-2,5-diyl; ring J represents 1,4-cyclohexylene or 1,4-phenylene, $Z_6$ represents —$CH_2CH_2$—, —$CO_2$—, or a covalent bond; $L_3$, $L_4$, and $L_5$ independently represent hydrogen atom or fluorine atom; c, d, e, f, and g are independently 0 or 1; and each of the elements in the general formulas may be its isotope.

14. A liquid crystal composition comprising, as a first component, at least one liquid crystalline compound defined in claim 1, as a second component, at least one compound selected from the group consisting of the compounds expressed by any one of the general formulas (2), (3), and (4)

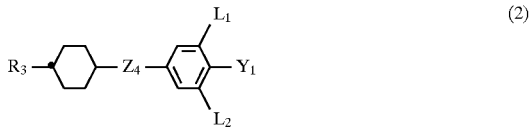  (2)

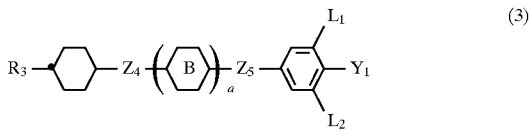  (3)

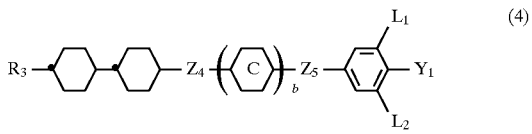  (4)

wherein $R_3$ represents an alkyl group having 1 to 10 carbon atoms in which group one or not-adjacent two or more methylene groups may be replaced by oxygen atom or —CH=CH—, and any hydrogen atom may be replaced by fluorine atom; $Y_1$ represents fluorine atom, chlorine atom, —$OCF_3$, —$OCF_2H$, —$CF_3$, —$CF_2H$, —$CFH_2$, —$OCF_2CF_2H$, or —$OCF_2CFHCF_3$; $L_1$, and $L_2$ independently represent hydrogen atom or fluorine atom; $Z_4$ and $Z_5$ independently represent —$CH_2CH_2$—, —$(CH_2)_4$-, —$CO_2$—, —$CF_2O$—, —$OCF_2$—, —CH=CH—, or a covalent bond; ring B represents 1,4-cyclohexylene, 1,3-dioxane-2,5-diyl, or 1,4-phenylene in which phenylene any hydrogen atom may be replaced by fluorine atom; ring C represents 1,4-cyclohexylene, or 1,4-phenylene in which phenylene any hydrogen atom may be replaced by fluorine atom; a and b are independently 0 or 1; and each of the elements in the general formulas may be its isotope, and as a third component, at least one compound selected from the group consisting of the compounds expressed by any one of the general formulas (7), (8), and (9)

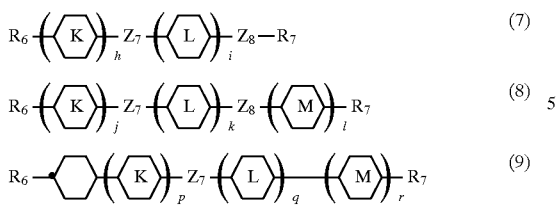

(7)

(8)

(9)

wherein $R_6$ and $R_7$ independently represent an alkyl group having 1 to 10 carbon atoms in which group one or not-adjacent two or more methylene groups may be replaced by oxygen atom or —CH=CH—, and any hydrogen atom may be replaced by fluorine atom; rings K, L, and M independently represent 1,4-cyclohexylene, pyrimidine-2,5-diyl, or 1,4-phenylene in which phenylene hydrogen atom may be replaced by fluorine atom; $Z_7$ and $Z_8$ independently represent —C≡C—, —CO$_2$—, —CH$_2$CH$_2$—, —CH=CH—, or a covalent bond; h to l, and p to r are independently 0 or 1; and each of the elements in the general formulas may be its isotope.

15. A liquid crystal composition comprising, as a first component, at least one liquid crystalline compound defined in claim 1, as a second component, at least one compound selected from the group consisting of the compounds expressed by the general formula (5) or (6)

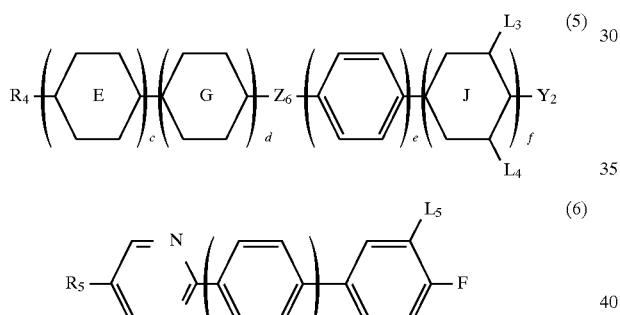

wherein $R_4$ and $R_5$ independently represent an alkyl group having 1 to 10 carbon atoms in which group one or not-adjacent two or more methylene groups may be replaced by oxygen atom or —CH=CH—, and any hydrogen atom may be replaced by fluorine atom; $Y_2$ represents —CN group or —C≡C—CN; ring E represents 1,4-cyclohexylene, 1,4-phenylene, 1,3-dioxane-2,5-diyl, or pyrimidine-2,5-diyl; ring G represents 1,4-cyclohexylene, 1,4-phenylene in which phenylene hydrogen atom may be replaced by fluorine atom, or pyrimidine-2,5-diyl; ring J represents 1,4-cyclohexylene or 1,4-phenylene, $Z_6$ represents —CH$_2$CH$_2$—, —CO$_2$—, or a covalent bond; $L_3$, $L_4$, and $L_5$ independently represent hydrogen atom or fluorine atom; c, d, e, f, and g are independently 0 or 1; and each of the elements in the general formulas may be its isotope, and as a third component, at least one compound selected from the group consisting of the compounds expressed by any one of the general formulas (7), (8), and (9)

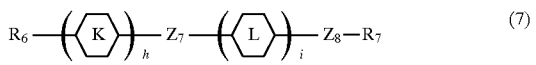

(7)

-continued

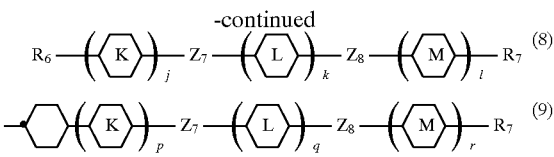

(8)

(9)

wherein $R_6$ and $R_7$ independently represent an alkyl group having 1 to 10 carbon atoms in which group one or not-adjacent two or more methylene groups may be replaced by oxygen atom or —CH=CH—, and any hydrogen atom may be replaced by fluorine atom; rings K, L, and M independently represent 1,4-cyclohexylene, pyrimidine-2,5-diyl, or 1,4-phenylene in which phenylene hydrogen atom may be replaced by fluorine atom; $Z_7$ and $Z_8$ independently represent —C≡C—, —CO$_2$—, —CH$_2$CH$_2$—, —CH=CH—, or a covalent bond; h to l, and p to r are independently 0 or 1; and each of the elements in the general formulas may be its isotope.

16. A liquid crystal composition comprising, as a first component, at least one liquid crystalline compound defined in claim 1, as a part of a second component, at least one compound selected from the group consisting of the compounds expressed by any one of the general formulas (2), (3), and (4)

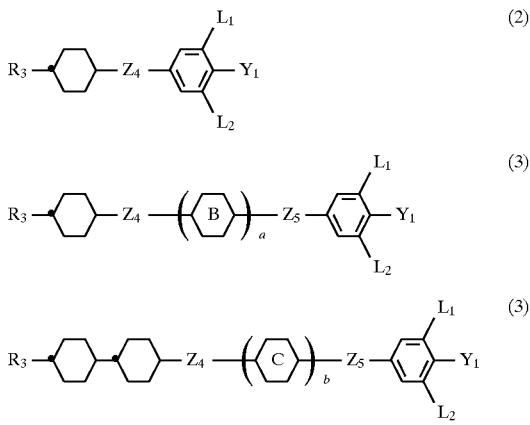

(2)

(3)

(3)

wherein $R_3$ represents an alkyl group having 1 to 10 carbon atoms in which group one or not-adjacent two or more methylene groups may be replaced by oxygen atom or —CH=CH—, and any hydrogen atom may be replaced by fluorine atom; $Y_1$ represents fluorine atom, chlorine atom, —OCF$_3$, —OCF$_2$H, —CF$_3$, —CF$_2$H, —CFH$_2$, —OCF$_2$CF$_2$H, or —OCF$_2$CFHCF$_3$; $L_1$ and L2 independently represent hydrogen atom or fluorine atom; $Z_4$ and $Z_5$ independently represent —CH$_2$CH$_2$—, —(CH$_2$)$_4$-, —CO$_2$—, —CF$_2$O—, —OCF$_2$—, —CH=CH—, or a covalent bond; ring B represents 1,4-cyclohexylene, 1,3-dioxane-2,5-diyl, or 1,4-phenylene in which phenylene any hydrogen atom may be replaced by fluorine atom; ring C represents 1,4-cyclohexylene, or 1,4-phenylene in which phenylene any hydrogen atom may be replaced by fluorine atom; a and b are independently 0 or 1; and each of the elements in the general formulas may be its isotope, as another part of the second component, at least one compound selected from the group consisting of the compounds expressed by the general formula (5) or (6)

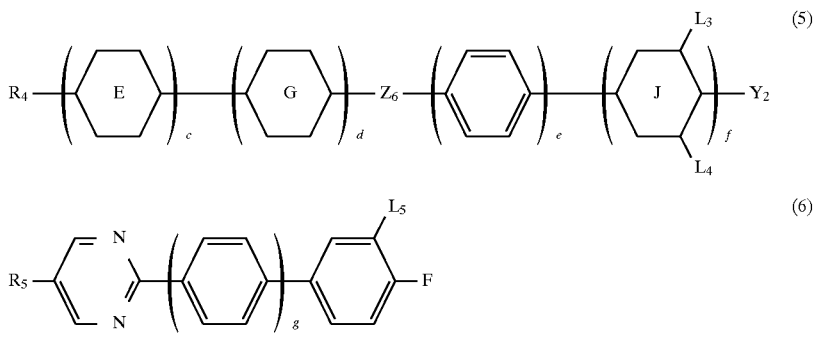

wherein $R_4$ and $R_5$ independently represent an alkyl group having 1 to 10 carbon atoms in which group one or not-adjacent two or more methylene groups may be replaced by oxygen atom or —CH=CH—, and any hydrogen atom may be replaced by fluorine atom; $Y_2$ represents —CN group or —C≡C—CN; ring E represents 1,4-cyclohexylene, 1,4-phenylene, 1,3-dioxane-2,5-diyl, or pyrimidine-2,5-diyl; ring G represents 1,4-cyclohexylene, 1,4-phenylene in which phenylene hydrogen atom may be replaced by fluorine atom, or pyrimidine-2,5-diyl; ring J represents 1,4-cyclohexylene or 1,4-phenylene, $Z_6$ represents —CH$_2$CH$_2$—, —CO$_2$—, or a covalent bond; $L_3$, $L_4$, and $L_5$ independently represent hydrogen atom or fluorine atom; c, d, e, f, and g are independently 0 or 1; and each of the elements in the general formulas may be its isotope, and as a third component, at least one compound selected from the group consisting of the compounds expressed by any one of the general formulas (7), (8), and (9)

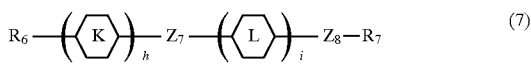

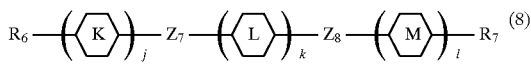

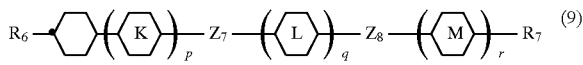

wherein R6 and $R_7$ independently represent an alkyl group having 1 to 10 carbon atoms in which group one or not-adjacent two or more methylene groups may be replaced by oxygen atom or —CH≡CH—, and any hydrogen atom may be replaced by fluorine atom; rings K, L, and M independently represent 1,4-cyclohexylene, pyrimidine-2,5-diyl, or 1,4-phenylene in which phenylene hydrogen atom may be replaced by fluorine atom; $Z_7$ and $Z_8$ independently represent —C≡C—, —CO$_2$—, —CH$_2$CH$_2$—, —CH=CH—, or a covalent bond; h to l, and p to r are independently 0 or 1; and each of the elements in the general formulas may be its isotope.

17. The liquid crystal composition according to claim 11 wherein the liquid crystal composition comprises an optically active compound.

18. The liquid crystal composition according to claim 12 wherein the liquid crystal composition further comprises an optically active compound.

19. The liquid crystal composition according to claim 13 wherein the liquid crystal composition further comprises an optically active compound.

20. The liquid crystal composition according to claim 14 wherein the liquid crystal composition further comprises an optically active compound.

21. The liquid crystal composition according to claim 15 wherein the liquid crystal composition further comprises an optically active compound.

22. The liquid crystal composition according to claim 16 wherein the liquid crystal composition further comprises an optically active compound.

23. A liquid crystal display device comprising the liquid crystal composition defined in claim 11 or 17.

24. A liquid crystal display device comprising the liquid crystal composition defined in claim 12 or 18.

25. A liquid crystal display device comprising the liquid crystal composition defined in claim 13 or 19.

26. A liquid crystal display,device comprising the liquid crystal composition defined in claim 14 or 20.

27. A liquid crystal display device comprising the liquid crystal composition defined in claim 15 or 21.

28. A liquid crystal display device comprising the liquid crystal composition defined in claim 16 or 22.

* * * * *